(12) United States Patent
Super et al.

(10) Patent No.: US 11,312,949 B2
(45) Date of Patent: *Apr. 26, 2022

(54) ENGINEERED HEME-BINDING COMPOSITIONS AND USES THEREOF

(71) Applicant: PRESIDENT AND FELLOWS OF HARVARD COLLEGE, Cambridge, MA (US)

(72) Inventors: Michael Super, Lexington, MA (US); Alexander L. Watters, North Andover, MA (US); Philip T. Snell, Lexington, MA (US); Donald E. Ingber, Boston, MA (US)

(73) Assignee: PRESIDENT AND FELLOWS OF HARVARD COLLEGE, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/661,595

(22) Filed: Oct. 23, 2019

(65) Prior Publication Data

US 2020/0248158 A1 Aug. 6, 2020

Related U.S. Application Data

(63) Continuation of application No. 15/968,116, filed on May 1, 2018, now Pat. No. 10,501,729, which is a continuation of application No. 14/892,252, filed as application No. PCT/US2014/038945 on May 21, 2014, now Pat. No. 9,988,617.

(60) Provisional application No. 61/825,707, filed on May 21, 2013.

(51) Int. Cl.
| | |
|---|---|
| *C12N 9/96* | (2006.01) |
| *C12N 9/26* | (2006.01) |
| *A61K 38/00* | (2006.01) |
| *C07K 14/805* | (2006.01) |

(52) U.S. Cl.
CPC ............ *C12N 9/2474* (2013.01); *A61K 38/00* (2013.01); *C07K 14/805* (2013.01); *C12N 9/96* (2013.01); *C12Y 302/01035* (2013.01)

(58) Field of Classification Search
None
See application file for complete search history.

(56) References Cited

U.S. PATENT DOCUMENTS

| | | |
|---|---|---|
| 4,425,330 A | 1/1984 | Norcross et al. |
| 5,137,810 A | 8/1992 | Sizemore |
| 5,270,199 A | 12/1993 | Ezekowitz |
| 5,273,884 A | 12/1993 | Gale et al. |
| 5,405,832 A | 4/1995 | Potempa |
| 5,474,904 A | 12/1995 | Potempa et al. |
| 5,545,820 A | 8/1996 | Gatehouse |
| 5,585,349 A | 12/1996 | Potempa |
| 5,783,179 A | 7/1998 | Nestor, Jr. et al. |
| 5,874,238 A | 2/1999 | Potempa et al. |
| 5,951,976 A | 9/1999 | Segal |
| 6,057,295 A | 5/2000 | Caretto et al. |
| 6,117,977 A | 9/2000 | Lasky |
| 6,225,046 B1 | 5/2001 | Vesey |
| 6,376,473 B1 | 4/2002 | Audonnet et al. |
| 6,429,192 B1 | 8/2002 | Laursen |
| 6,471,968 B1 | 10/2002 | Baker et al. |
| 6,503,761 B1 | 1/2003 | Koenig |
| 6,528,618 B1 | 3/2003 | Fridkin et al. |
| 6,528,624 B1 | 3/2003 | Idusogie |
| 6,562,784 B1 | 5/2003 | Thiel |
| 6,703,219 B1 | 3/2004 | Potempa et al. |
| 6,733,753 B2 | 5/2004 | Boone |
| 6,846,649 B1 | 1/2005 | Thiel |
| 6,900,292 B2 | 5/2005 | Sun |
| 7,182,945 B2 | 2/2007 | Fridkin et al. |
| 7,202,207 B2 | 4/2007 | Thiel |
| 7,211,396 B2 | 5/2007 | Uttenthal |
| 7,226,429 B2 | 6/2007 | Tullis |
| 7,439,224 B2 | 10/2008 | Thiel |
| 7,462,596 B2 | 12/2008 | Larsen |
| 7,465,447 B2 | 12/2008 | Gillies et al. |
| 7,566,694 B2 | 7/2009 | Rider |
| 7,629,440 B2 | 12/2009 | Segal et al. |
| 7,695,937 B2 | 4/2010 | Baum |
| 7,763,436 B2 | 7/2010 | Das |
| 8,013,120 B2 | 9/2011 | Du Clos et al. |
| 8,080,245 B2 | 12/2011 | Visintin |
| 8,084,275 B2 | 12/2011 | Hirai |
| 8,088,596 B2 | 1/2012 | Zeng |
| 8,415,118 B2 | 4/2013 | Huang |

(Continued)

FOREIGN PATENT DOCUMENTS

| | | |
|---|---|---|
| CA | 2645888 A1 | 6/2007 |
| CN | 102325882 A | 1/2012 |

(Continued)

OTHER PUBLICATIONS

Agrawal et al., "C-reactive protein mutant that does not bind to phosphocholine and pneumococcal C-polysaccharide", J. Immunol. 169(6):3217-3222 (2002).

Arakawa et al., "Elution of antibodies from a Protein-A column by aqueous arginine solutions", Protein Expression and Purification 36:244-248 (2004).

Armour et al., "Recombinant human IgG molecules lacking Fcγ receptor I binding and monocyte triggering activities", European Journal of Immunology 29:2613-2624 (1999).

Ashkenazi et al., "Immunoadhesins as research tools and therapeutic agents", Current Opinion in Immunology 9:195-200 (1997).

Azevedo et al., "Horseradish peroxidase: a valuable tool in biotechnology," Biotechnology Annual Review 9:199-247 (2003).

(Continued)

*Primary Examiner* — Hope A Robinson
(74) *Attorney, Agent, or Firm* — Nixon Peabody LLP; David S. Resnick; Nicole D. Kling

(57) ABSTRACT

Described herein are heme-binding compositions and methods relating to their use, for example methods of treatment of sepsis and rhabdomyolysis.

18 Claims, 4 Drawing Sheets
Specification includes a Sequence Listing.

(56) References Cited

U.S. PATENT DOCUMENTS

| | | | |
|---|---|---|---|
| 8,470,555 B2 | 6/2013 | Suzuki et al. | |
| 8,598,324 B2 | 12/2013 | Rider | |
| 9,150,631 B2 | 10/2015 | Super et al. | |
| 9,644,021 B2 | 5/2017 | Wang et al. | |
| 9,988,617 B2* | 6/2018 | Super | A61K 38/00 |
| 10,501,729 B2* | 12/2019 | Super | A61P 31/04 |
| 2002/0147311 A1 | 10/2002 | Gillies et al. | |
| 2003/0162248 A1 | 8/2003 | Wakamiya | |
| 2003/0166878 A1 | 9/2003 | Nishiya | |
| 2003/0180814 A1 | 9/2003 | Hodges et al. | |
| 2004/0018611 A1 | 1/2004 | Ward et al. | |
| 2004/0229212 A1 | 11/2004 | Thiel | |
| 2005/0014932 A1 | 1/2005 | Imboden | |
| 2005/0037949 A1 | 2/2005 | O'Brien | |
| 2006/0040362 A1 | 2/2006 | Wakamiya | |
| 2006/0104975 A1 | 5/2006 | Geijtenbeek | |
| 2006/0177879 A1 | 8/2006 | Mayes | |
| 2006/0188963 A1 | 8/2006 | Kongerslev | |
| 2006/0251580 A1 | 11/2006 | Keppler | |
| 2007/0031819 A1 | 2/2007 | Koschwanez et al. | |
| 2007/0049532 A1 | 3/2007 | Feige et al. | |
| 2007/0072247 A1 | 3/2007 | Wong | |
| 2007/0122850 A1 | 5/2007 | Teng | |
| 2007/0184463 A1 | 8/2007 | Molho et al. | |
| 2007/0224640 A1 | 9/2007 | Caldwell | |
| 2007/0231833 A1 | 10/2007 | Arcidiacono et al. | |
| 2007/0269818 A1 | 11/2007 | Savage | |
| 2008/0014576 A1 | 1/2008 | Jovanovich et al. | |
| 2008/0056949 A1 | 3/2008 | Lee et al. | |
| 2008/0108120 A1 | 5/2008 | Cho et al. | |
| 2008/0156736 A1 | 7/2008 | Hirai | |
| 2008/0182793 A1 | 7/2008 | Baum | |
| 2008/0193965 A1 | 8/2008 | Zeng | |
| 2008/0260738 A1 | 10/2008 | Moore | |
| 2008/0300188 A1 | 12/2008 | Yang et al. | |
| 2009/0078614 A1 | 3/2009 | Varghese et al. | |
| 2009/0175797 A1 | 7/2009 | Warren et al. | |
| 2009/0181041 A1 | 7/2009 | Holgersson | |
| 2009/0220932 A1 | 9/2009 | Ingber | |
| 2009/0252729 A1 | 10/2009 | Farrington et al. | |
| 2009/0269843 A1 | 10/2009 | Blume et al. | |
| 2009/0297516 A1 | 12/2009 | Mayo | |
| 2010/0044232 A1 | 2/2010 | Lin et al. | |
| 2010/0055675 A1 | 3/2010 | Kumamoto et al. | |
| 2010/0266558 A1 | 10/2010 | Zipori | |
| 2010/0323342 A1 | 12/2010 | Gomez et al. | |
| 2010/0323429 A1 | 12/2010 | Hu | |
| 2010/0331240 A1 | 12/2010 | Michelow | |
| 2011/0027267 A1 | 2/2011 | Kyneb | |
| 2011/0053145 A1 | 3/2011 | Takakura | |
| 2011/0053250 A1 | 3/2011 | Takakura | |
| 2011/0065095 A1 | 3/2011 | Kida et al. | |
| 2011/0159000 A1 | 6/2011 | Silverman | |
| 2011/0183398 A1 | 7/2011 | Dasaratha | |
| 2011/0281792 A1 | 11/2011 | Zion | |
| 2012/0100140 A1 | 4/2012 | Reyes et al. | |
| 2012/0164628 A1 | 6/2012 | Duffin | |
| 2013/0029428 A1 | 1/2013 | Kim et al. | |
| 2013/0035283 A1 | 2/2013 | Super | |
| 2013/0072445 A9 | 3/2013 | Du Clos et al. | |
| 2014/0227723 A1 | 8/2014 | Ingber et al. | |
| 2014/0249087 A1 | 9/2014 | Warren et al. | |
| 2015/0173883 A1 | 6/2015 | Ingber et al. | |

FOREIGN PATENT DOCUMENTS

| | | | |
|---|---|---|---|
| EP | 0375736 B1 | 5/1998 | |
| EP | 0861667 A2 | 8/2001 | |
| EP | 0915970 B1 | 9/2004 | |
| EP | 1862541 A1 | 12/2007 | |
| EP | 2267151 A1 | 12/2010 | |
| EP | 1812459 B1 | 3/2011 | |
| JP | S54-18198 A | 2/1979 | |
| JP | S60-500548 A | 4/1985 | |
| JP | S63-315953 A | 12/1988 | |
| JP | H04130274 A | 5/1992 | |
| JP | 2002-165591 A | 6/2002 | |
| JP | 2002-517513 A | 6/2002 | |
| JP | 2006-517512 A | 7/2006 | |
| JP | 2008-535872 A | 9/2008 | |
| JP | 2010122205 A | 6/2010 | |
| JP | 2010268800 A | 12/2010 | |
| WO | 84/02193 A1 | 6/1984 | |
| WO | 2000006603 A1 | 2/2000 | |
| WO | 2001/003737 A1 | 1/2001 | |
| WO | 2002/032292 A2 | 4/2002 | |
| WO | 2003/014150 A2 | 2/2003 | |
| WO | 2003/054164 A2 | 7/2003 | |
| WO | 2004/018698 A2 | 3/2004 | |
| WO | 2005092925 A2 | 10/2005 | |
| WO | 2006/018428 A2 | 2/2006 | |
| WO | 2006/108417 A2 | 10/2006 | |
| WO | 2007/001332 A2 | 1/2007 | |
| WO | 2006/044650 A2 | 4/2007 | |
| WO | 2007/044642 A2 | 4/2007 | |
| WO | 2007/111496 A1 | 10/2007 | |
| WO | 2008/130618 A1 | 10/2008 | |
| WO | 2009/040048 A2 | 4/2009 | |
| WO | 2009/062195 A2 | 5/2009 | |
| WO | 2009/119722 A1 | 10/2009 | |
| WO | 2009/123347 A1 | 10/2009 | |
| WO | 2009/126346 A2 | 10/2009 | |
| WO | 2010078966 A1 | 7/2010 | |
| WO | 2011/084749 A1 | 7/2011 | |
| WO | 2011/090954 A2 | 7/2011 | |
| WO | 2011/091037 A2 | 7/2011 | |
| WO | 2011/103144 A1 | 8/2011 | |
| WO | 2012/019178 A2 | 2/2012 | |
| WO | 2012/050874 A2 | 4/2012 | |
| WO | 2012/100099 A2 | 7/2012 | |
| WO | 2012/135834 A2 | 10/2012 | |
| WO | 2012142515 A2 | 10/2012 | |
| WO | 2013/012924 A2 | 1/2013 | |
| WO | 2013/130875 A1 | 9/2013 | |
| WO | 2014/144325 A1 | 9/2014 | |

OTHER PUBLICATIONS

Bangs Laboratories, Inc., "Protein Coated Microspheres", Tech. Note #51 (1997). (4 pages).

Bayston et al., "Bacterial endotoxin and current concepts in the diagnosis and treatment of endotoxaemia", Journal of Medical Microbiology 31:73-83 (1990).

Barnum et al., "Comparative Studies on the Binding Specificities of C-Reactive Protein (CRP) and HOPC 8", Annals of the New York Academy of Sciences 389:431-434 (1982).

Bossola et al., "Circulating Bacterial-Derived DNA Fragments and Markers of Inflammation in Chronic Hemodialysis Patients", Clinical Journal of the American Society of Nephrology 4:379-385 (2009).

Brooks et al., "Expression and secretion of ficolin β by porcine neutrophils", Biochimica et Biophysica Acta 1624:36-45 (2003).

Brouwer et al., "Mannose-Binding Lectin (MBL) Facilitates Opsonophagocytosis of Yeasts but Not of Bacteria despite MBL Binding", The Journal of Immunology 180:4124-4132 (2008).

Casey et al., "The acute-phase reactant C-Reactive protein binds to phosphorylcholine-expressing Neisseria meningitidis and increased uptake by human phagocytes", Infection and Immunity 76(3): 12998-1304 (2008).

Castle et al., "The binding of 125I-labeled concanavalin A to the cell surface of rabbit peritoneal polymorphonuclear leucocytes." Biochemical Medicine 28(1):1-15 (1982).

Chamow et al., "Immunoadhesins: principles and applications", Trends Biotechnology 14:52-60 (1996).

Chang et al., "Crystallization and Preliminary X-ray Analysis of a Trimeric Form of Human Mannose Binding Protein", Journal of Molecular Biology 241:125-127 (1994).

Chen et al., "Fabrication of an Oriented Fc-Fused Lectin Microarray through Boronate Formation", Angewandte Chemie International Edition 47:8627-8630 (2008).

(56) References Cited

OTHER PUBLICATIONS

Chuang et al., "Computational prediction of N-linked glycosylation incorporating structural properties and patterns," Bioinformatics. Sep 1; 28(17): 2249-2255 (2012).
Culley et al., "C-reactive protein binds to phosphorylated carbohydrates", Glycobiology 10(1):59-65 (2000).
Dumont et al., "Monomeric Fc Fusions: Impact on Pharmacokinetic and Biological Activity of Protein Therapeutics", Biodrugs 20(3):151-160 (2006).
Feng et al., "Identification of carbohydrates on the surface membrane of pathogenic and nonpathogenic piscine haemoflagellates, Cryptobia salmositica, C. bullocki and C. catostomi (Kinetoplastida)." Diseases of Aquatic Organisms 32(3):201-209 (1998).
Foster, "Immune Evasion By Staphylococci", Nature 3:948-958 (2005).
Fox et al., "Single amino acid substitutions on the surface of *Escherichia coli* maltose-binding protein can have a profound impact on the solubility of fusion proteins", Protein Science 10:622-630 (2001).
Frakking et al., "Safety and phamacokinetics of plasma-derived mannose-binding lectin (MBL) substitution in children with chemotherapy-induced neutropaenia", European Journal of Cancer 45:505-512 (2009).
Garred et al., "Mannose-binding lectin and its genetic variants", Genes and Immunity 7:85-94 (2006).
Gouin et al., "Multimeric Lactoside "Click Clusters" as Tools to Investigate the Effect of Linker Length in Specific Interactions with Peanut Lectin, Galectin-1, and -3", ChemBioChem 11:1430-1442 (2010).
Grogl et al., "Leishmania braziliensis: Protein, Carbohydrate, and Antigen Differences between Log Phase and Stationary Phase Promastigotes in Vitro", Experimental Parasitology 63:352-359 (1987).
Hinton et al., "Engineered Human IgG Antibodies with Longer Serum Half-lives in Primates", The Journal of Biological Chemistry 279(8):6213-6216 (2004).
Hohenester, "Tackling the Legs of Mannan-Binding Lectin", Structure 19:1538-1540 (2011).
Holmskov et al., "Affinity and kinetic analysis of the bovine plasma C-type lectin collectin-43 (CL-43) interacting with mannan", FEBS Letters 393:314-316 (1996).
Huang et al., "Integrated microfluidic system for rapid screening of CRP aptamers utilizing systematic evolution of ligands by exponential enrichment (SELEX)", Biosensors and Bioelectronics 25:1761-1766 (2010).
Huang et al., "Porcine DC-SIGN: Molecular cloning, gene structure, tissue distribution and binding characteristics", Developmental and Comparative Immunology 33:464-480 (2009).
Hwang et al., "The Pepper Mannose-Binding Lectin Gene CaMBL1 Is Required to Regulate Cell Death and Defense Responses to Microbial Pathogens", Plant Physiology 155:447-463 (2011).
Idusogie et al., "Engineered Antibodies with Increased Activity to Recruit Complement", The Journal of Immunology 166:2571-2575 (2001).
Ilyas et al., "High glucose disrupts oligosaccharide recognition function via competitive inhibition: a potential mechanism for immune dysregulation in diabetes mellitus", Immunobiology 216(1-2) 126-131 (2011).
Invivo Gen Insight, "IgG-Fc Engineering for Therapeutic Use", (2006). (4 pages).
Jack et al., "Mannose-binding lectin: targeting the microbial world for complement attack and opsonophagocytosis", Immunological Reviews 180:86-99 (2001).
Jarva et al., "*Streptococcus pneumoniae* Evades Complement Attack and Opsonophagocytosis by Expressing the pspC Locus-Encoded Hie Protein That Binds to Short Consensus Repeats 8-11 of Factor H", The Journal of Immunology 168:1886-1894(2002).

Kang et al., "The human macrophage mannose receptor directs *Mycobacterium tuberculosis* lipoarabinomanan-mediated phagosome biogenesis", The Journal of Experimental Medicine 202(7):987-999 (2005).
Keen et al., "Interrelationship Between pH and Surface Growth of Nitrobacter", Soil Biology and Biochemistry 19(6):665-672 (1987).
Kehres, "A kinetic model for binding protein-mediated arabinose transport", Protein Science 1:1661-1665 (1992).
Kjaer et al., "M-ficolin binds selectively to the capsular polysaccharides of *Streptococcus pneumoniae* serotypes 19B and 19C and of a *Streptococcus mitis* strain", Infect Immun 81(2) 452-459 (2013).
Krarup et al., "Simultaneous Activation of Complement and Coagulation by MBL-Associated Serine Protease 2", PLoS ONE 2(7):e623 (2007). (8 pages).
Lee et al., "Carbohydrate-binding properties of human neo-CRP and its relationship to phosphorylcholine-binding site", Glycobiology 13(1):11-21 (2003).
Linehan et al., "Endogenous ligands of carbohydrate recognition domains of the mannose receptor in murine macrophages, endothelial cells and secretory cells; potential relevance to inflammation and immunity", European Journal of Immunology 31:1857-1866 (2001).
Loosdrecht et al., "Influence of Interfaces on Microbial Activity", Microbiological Reviews 54(1):75-87 (1990).
Matsushita et al., "Activation of the Classical Complement Pathway by Mannose-binding Protein in Association with a Novel C1s-like Serine Protease", Journal of Experimental Medicine 176(6):1497-1502 (1992).
Michelow et al., "A Novel L-ficolin/Mannose-binding Lectin Chimeric Molecule with Enhanced Activity against Ebola Virus", The Journal of Biological Chemistry 285(32):24729-24739 (2010).
Mold et al., "Binding of Human C-Reactive Protein to Bacteria", Infection and Immunity 38(1):392-395 (1982).
Nadesalingam et al., "Mannose-Binding Lectin Recognizes Peptidoglycan via the N-acetyl Glucosamine Moiety, and Inhibits Ligand-Induced Proinflammatory Effect and Promotes Chemokine Production by Macrophages", The Journal of Immunology 175:1785-1794 (2005).
Nakamura et al., "Characterization of the interaction between serum mannan-binding protein and nucleic acid ligands", Journal of Leukocyte Biology 86:737-748 (2009).
Larsen et al., "A Central Role for Free Heme in the Pathogenesis of Severe Sepsis", Sci. Transl. Med., 2(51), p. 51ra71, 2010.
Saifuddin et al., "Interaction of mannose-binding lectin with primary isolates of human immunodeficiency virus type 1." Journal of General Virology 81.4 (2000): 949-955.
Gentle et al., "Direct production of proteins with N-terminal cysteine for site-specific conjugation." Bioconjugate chemistry 15.3 (2004): 658-663.
Witus et al., "Site-specific protein bioconjugation via a pyridoxal 5'-phosphate-mediated N-terminal transamination reaction." Current protocols in chemical biology 2.2 (2010): 125-134.
Bowie et al., "Deciphering the Message in Protein Sequences: Tolerance to Amino Acid Substitutions", Science 247(4948) 1306-1310 (1990).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" The Journal of Cell Biology, 111, 2129-2138, (1990).
Lazar et al., "Transforming Growth Factor alpha: Mutation of Aspartic Acid 47 and Leucine 48 Results in Different Biological Activities", Molecular and Cellular Biology, 8(3), 1247-1252, (1988).
Sazinsky et al., "Aglycosylated immunoglobulin G1 variants productively engage activating Fc receptors", Proceedings of the National Academy of Sciences 105(51) 20167-20172, (2008).
Wallis, "Interactions between mannose-binding lectin and MASPs during complement activation by the lectin pathway", Immunobiology 212 (4-5), 289-299 (2007).
Neth et al., "Enhancement of Complement Activation and Opsonophagocytosis by Complexes of Mannose-Binding Lectin

(56) References Cited

OTHER PUBLICATIONS with Mannose-Binding Lectin-Associated Serine Protease After Binding to *Staphylococcus aureus*", The Journal of Immunology 169:4430-4436 (2002).
Neth et al., "Mannose-Binding Lectin Binds to a Range of Clinically Relevant Microorganisms and Promotes Complement Deposition", Infection and Immunity 68(2):688-693 (2000).
Nisnevitch et al., "The solid phase in affinity chromatography: strategies for antibody attachment", Journal of Biochemical and Biophysical Methods 49:467-480 (2001).
Ogden et al., "C1q and Mannose Binding Lectin Engagement of Cell Surface Calreticulin and CD91 Initiates Macropinocytosis and Uptake of Apoptotic Cells", The Journal of Experimental Medicine 194(6):781-795 (2001).
Perham, "Domains, Motifs, and Linkers in 2-Oxo Acid Dehydrogenase Multienzyme Complexes: A Paradigm in the Design of a Multifunction Protein", Biochemistry 30(35):8501-8512 (1991).
Presanis et al., "Biochemistry and genetics of mannan-binding lectin (MBL)", Biochemical Society Transactions 31(4):748-752 (2003).
Rouhandeh et al., "Surface membrane redistribution and stabilization of concanavalin A-specific receptors following Yaba tumor poxvirus infection." Biochimica et Biophysica Acta (BBA)-Biomembranes 600(2):1301-312 (1980).
Rutishauser et al., "Amino Acid Sequence of The Fc Region of a Human γG Immunoglobulin", Biochemistry 61:1414-1421 (1968).
Safarik et al., "The application of magnetic separations in applied microbiology", Journal of Applied Bacteriology 78:575-585 (1995).
Schmidt, "Fusion proteins as biopharmaceuticals—Applications and challenges", Current Opinion in Drug Discovery & Development 12(2):284-295 (2009).
Sheriff et al., "Human mannose-binding protein carbohydrate recognition domain trimerizes through a triple alpha-helical coiled-coil", Nat Struct Biol 1(11) 789-794 (1994).
Shields et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry 276(9):6591-6604 (2001).
Shoulders et al., "Collagen structure and stability." Annual Review of Biochemistry 78(1):929-958 (2009).
Sibille et al., "Comparison of serological tests for the diagnosis of feline immunodeficiency virus infection of cats", Veterinary Microbiology 45:259-267 (1995).
Sprong et al., "Mannose-Binding Lectin Is a Critical Factor in Systemic Complement Activation during Meningococcal Septic Shock", Clinical Infectious Diseases 49:1380-1386 (2009).
Steentoft et al. "Precision mapping of the human O—GalNAc glycoproteome through SimpleCell technology," EMBO J. May 15;32(10):1478-88. (2013).
Steurer et al., "Ex Vivo Coating of Islet Cell Allografts with Murine CTLA4/Fc Promotes Graft Tolerance", The Journal of Immunology 155:1165-1174 (1995).
Stuart et al., "Mannose-Binding Lectin-Deficient Mice Display Defective Apoptotic Cell Clearance but No Autoimmune Phenotype", The Journal of Immunology 174:3220-3226 (2005).
Szalai, "The biological functions of C-reactive protein", Vascular Pharmacology 39:105-107 (2002).
Takahashi et al., "Mannose-binding lectin and its associated proteases (MASPs) mediate coagulation and its deficiency is a risk factor in developing complications from infection, including disseminated intravascular coagulation", Immunobiology 216(1-2):96-102 (2011).
Terai et al., "Relationship between gene polymorphisms of mannose-binding lectin (MBL) and two molecular forms of MBL", European Journal of Immunology 33:2755-2763 (2003).
Thiel et al., "A second serine protease associated with mannan-binding lectin that activates complement", Nature 386:506-510 (1997).
Vaccaro et al., "Engineering the Fc region of immunoglobulin G to modulate in vivo antibody levels", Nature Biotechnology 23(10):1283-1288 (2005).
Ward et al., "Characterization of Humanized Antibodies Secreted by Aspergillus niger", Applied and Environmental Microbiology 70(5):2567-2576 (2004).
Warwick et al., "Use of Quantitative 16S Ribosomal DNA Detection for Diagnosis of Central Vascular Catheter-Associated Bacterial Infection", Journal of Clinical Microbiology 42(4):1402-1408 (2004).
Witus et al., "Identification of Highly Reactive Sequences For PLP-Mediated Bioconjugation Using a Combinatorial Peptide Library", Journal of the American Chemical Society 132:16812-16817 (2010).
Wong et al., "Bioinspired self-repairing slippery surfaces with pressure-stable omniphobicity", Nature 477:443-447 (2011).
Wriggers et al., "Control of Protein Functional Dynamics by Peptide Linkers", Biopolymers (Peptide Science) 80:736-746 (2005).
Xia et al., "Combined microfluidic-micromagnetic separation of living cells in continuous flow", Biomed Microdevices 8:299-308 (2006).
Ye et al., "Surface display of a glucose binding protein", Journal of Molecular Catalysis B: Enzymatic 28:201-206 (2004).
Ying et al., "Soluble Monomeric IgG1 Fc", The Journal of Biological Chemistry 287(23):19399-19408 (2012).
Yung et al., "Micromagnetic-microfluidic blood cleansing device", Lab on a Chip 9:1171-1177 (2009).
Zettner et al., "Principles of competitive binding assays (saturation analyses). II. Sequential saturation", Clin Chem 20(1) 5-14 (1974).
Zettner et al., "Principles of competitive binding assays (saturation analysis). 1. Equilibrium techniques", Clin Chem 19(7) 699-705 (1973).
Zhavnerko et al., "Oriented Immobilization of C-Reactive Protein on Solid Surface for Biosensor Applications", Frontiers of Multifunctional Integrated Nanosystems 95-108 (2004).
Choma et al. "Design of a Heme-Binding Four-Helix Bundle", J. Am. Chem. Soc. 116:856-865 (1994).
Czajkowsky et al., "Fc-fusion proteins: new developments and future perspectives", EMBO Mol Med., 4(10):1015-1028 (2012).
Johnson et al. "Iron metabolism and the innate immune response to infection." Microbes and infection / Insitut Pasteur 14:207 (2012).
Lin et al. "Synergistic inflammation is induced by blood degradation products with microbial Toll-like receptor agonists and is blocked by hemopexin." The Journal of Infectious Diseases 202:624 (2010).
Lo et al., "High level expression and secretion of Fc-X fusion proteins in mammalian cells", Protein Engineering 11(6):495-500 (1998).
Mantuano et al., "The hemopexin domain of matrix metalloproteinase-9 activates cell signaling and promotes migration of schwann cells by binding to low-density lipoprotein receptor-related protein ", The Journal of Neuroscience 28(45):11571-11582 (2008).
Mauk et al. "An alternative view of the proposed alternative activities of hemopexin." Protein Science. 20:791 (2011).
Storch "Diagnostic virology." Clinical infectious diseases 31.3 (2000): 739-751.

* cited by examiner

SEQUENCE LISTING

<160> NUMBER OF SEQ ID NOS: 35

<210> SEQ ID NO 1
<211> LENGTH: 462
<212> TYPE: PRT
<213> ORGANISM: Homo sapiens

<400> SEQUENCE: 1

```
Met Ala Arg Val Leu Gly Ala Pro Val Ala Leu Gly Leu Trp Ser Leu
1               5                   10                  15

Cys Trp Ser Leu Ala Ile Ala Thr Pro Leu Pro Pro Thr Ser Ala His
            20                  25                  30

Gly Asn Val Ala Glu Gly Glu Thr Lys Pro Asp Pro Asp Val Thr Glu
        35                  40                  45

Arg Cys Ser Asp Gly Trp Ser Phe Asp Ala Thr Thr Leu Asp Asp Asn
    50                  55                  60

Gly Thr Met Leu Phe Phe Lys Gly Glu Phe Val Trp Lys Ser His Lys
65                  70                  75                  80

Trp Asp Arg Glu Leu Ile Ser Glu Arg Trp Lys Asn Phe Pro Ser Pro
                85                  90                  95

Val Asp Ala Ala Phe Arg Gln Gly His Asn Ser Val Phe Leu Ile Lys
            100                 105                 110

Gly Asp Lys Val Trp Val Tyr Pro Pro Glu Lys Lys Glu Lys Gly Tyr
        115                 120                 125

Pro Lys Leu Leu Gln Asp Glu Phe Pro Gly Ile Pro Ser Pro Leu Asp
    130                 135                 140

Ala Ala Val Glu Cys His Arg Gly Glu Cys Gln Ala Glu Gly Val Leu
145                 150                 155                 160

Phe Phe Gln Gly Asp Arg Glu Trp Phe Trp Asp Leu Ala Thr Gly Thr
                165                 170                 175

Met Lys Glu Arg Ser Trp Pro Ala Val Gly Asn Cys Ser Ser Ala Leu
            180                 185                 190

Arg Trp Leu Gly Arg Tyr Tyr Cys Phe Gln Gly Asn Gln Phe Leu Arg
        195                 200                 205

Phe Asp Pro Val Arg Gly Glu Val Pro Pro Arg Tyr Pro Arg Asp Val
    210                 215                 220

Arg Asp Tyr Phe Met Pro Cys Pro Gly Arg Gly His Gly His Arg Asn
225                 230                 235                 240

Gly Thr Gly His Gly Asn Ser Thr His His Gly Pro Glu Tyr Met Arg
                245                 250                 255
```

Cys Ser Pro His Leu Val Leu Ser Ala Leu Thr Ser Asp Asn His Gly
            260                 265                 270

Ala Thr Tyr Ala Phe Ser Gly Thr His Tyr Trp Arg Leu Asp Thr Ser
            275                 280                 285

Arg Asp Gly Trp His Ser Trp Pro Ile Ala His Gln Trp Pro Gln Gly
            290                 295                 300

Pro Ser Ala Val Asp Ala Ala Phe Ser Trp Glu Glu Lys Leu Tyr Leu
305                 310                 315                 320

Val Gln Gly Thr Gln Val Tyr Val Phe Leu Thr Lys Gly Gly Tyr Thr
            325                 330                 335

Leu Val Ser Gly Tyr Pro Lys Arg Leu Glu Lys Glu Val Gly Thr Pro
            340                 345                 350

His Gly Ile Ile Leu Asp Ser Val Asp Ala Ala Phe Ile Cys Pro Gly
            355                 360                 365

Ser Ser Arg Leu His Ile Met Ala Gly Arg Arg Leu Trp Trp Leu Asp
            370                 375                 380

Leu Lys Ser Gly Ala Gln Ala Thr Trp Thr Glu Leu Pro Trp Pro His
385                 390                 395                 400

Glu Lys Val Asp Gly Ala Leu Cys Met Glu Lys Ser Leu Gly Pro Asn
            405                 410                 415

Ser Cys Ser Ala Asn Gly Pro Gly Leu Tyr Leu Ile His Gly Pro Asn
            420                 425                 430

Leu Tyr Cys Tyr Ser Asp Val Glu Lys Leu Asn Ala Ala Lys Ala Leu
            435                 440                 445

Pro Gln Pro Gln Asn Val Thr Ser Leu Leu Gly Cys Thr His
450                 455                 460

<210> SEQ ID NO 2
<211> LENGTH: 233
<212> TYPE: PRT
<213> ORGANISM: Homo sapiens

<400> SEQUENCE: 2

Thr Pro Leu Pro Pro Thr Ser Ala His Gly Asn Val Ala Glu Gly Glu
1               5                   10                  15

Thr Lys Pro Asp Pro Asp Val Thr Glu Arg Cys Ser Asp Gly Trp Ser
            20                  25                  30

Phe Asp Ala Thr Thr Leu Asp Asp Asn Gly Thr Met Leu Phe Phe Lys
            35                  40                  45

Gly Glu Phe Val Trp Lys Ser His Lys Trp Asp Arg Glu Leu Ile Ser
    50                  55                  60

Glu Arg Trp Lys Asn Phe Pro Ser Pro Val Asp Ala Ala Phe Arg Gln
65                  70                  75                  80

Gly His Asn Ser Val Phe Leu Ile Lys Gly Asp Lys Val Trp Val Tyr
                85                  90                  95

Pro Pro Glu Lys Lys Glu Lys Gly Tyr Pro Lys Leu Leu Gln Asp Glu
            100                 105                 110

Phe Pro Gly Ile Pro Ser Pro Leu Asp Ala Ala Val Glu Cys His Arg
            115                 120                 125

Gly Glu Cys Gln Ala Glu Gly Val Leu Phe Phe Gln Gly Asp Arg Glu
    130                 135                 140

Trp Phe Trp Asp Leu Ala Thr Gly Thr Met Lys Glu Arg Ser Trp Pro
145                 150                 155                 160

Ala Val Gly Asn Cys Ser Ser Ala Leu Arg Trp Leu Gly Arg Tyr Tyr
                165                 170                 175

```
Cys Phe Gln Gly Asn Gln Phe Leu Arg Phe Asp Pro Val Arg Gly Glu
            180                 185                 190

Val Pro Pro Arg Tyr Pro Arg Asp Val Arg Asp Tyr Phe Met Pro Cys
        195                 200                 205

Pro Gly Arg Gly His Gly His Arg Asn Gly Thr Gly His Gly Asn Ser
    210                 215                 220

Thr His His Gly Pro Glu Tyr Met Arg
225                 230

<210> SEQ ID NO 3
<211> LENGTH: 674
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Ala Thr Pro Leu Pro Pro
225                 230                 235                 240

Thr Ser Ala His Gly Asn Val Ala Glu Gly Glu Thr Lys Pro Asp Pro
                245                 250                 255

Asp Val Thr Glu Arg Cys Ser Asp Gly Trp Ser Phe Asp Ala Thr Thr
            260                 265                 270

Leu Asp Asp Asn Gly Thr Met Leu Phe Phe Lys Gly Glu Phe Val Trp
        275                 280                 285

Lys Ser His Lys Trp Asp Arg Glu Leu Ile Ser Glu Arg Trp Lys Asn
```

```
                290                 295                 300
Phe Pro Ser Pro Val Asp Ala Ala Phe Arg Gln Gly His Asn Ser Val
305                 310                 315                 320
Phe Leu Ile Lys Gly Asp Lys Val Trp Val Tyr Pro Glu Lys Lys
                325                 330                 335
Glu Lys Gly Tyr Pro Lys Leu Leu Gln Asp Glu Phe Pro Gly Ile Pro
                340                 345                 350
Ser Pro Leu Asp Ala Ala Val Glu Cys His Arg Gly Glu Cys Gln Ala
                355                 360                 365
Glu Gly Val Leu Phe Phe Gln Gly Asp Arg Glu Trp Phe Trp Asp Leu
                370                 375                 380
Ala Thr Gly Thr Met Lys Glu Arg Ser Trp Pro Ala Val Gly Asn Cys
385                 390                 395                 400
Ser Ser Ala Leu Arg Trp Leu Gly Arg Tyr Tyr Cys Phe Gln Gly Asn
                405                 410                 415
Gln Phe Leu Arg Phe Asp Pro Val Arg Gly Glu Val Pro Pro Arg Tyr
                420                 425                 430
Pro Arg Asp Val Arg Asp Tyr Phe Met Pro Cys Pro Gly Arg Gly His
                435                 440                 445
Gly His Arg Asn Gly Thr Gly His Gly Asn Ser Thr His His Gly Pro
                450                 455                 460
Glu Tyr Met Arg Cys Ser Pro His Leu Val Leu Ser Ala Leu Thr Ser
465                 470                 475                 480
Asp Asn His Gly Ala Thr Tyr Ala Phe Ser Gly Thr His Tyr Trp Arg
                485                 490                 495
Leu Asp Thr Ser Arg Asp Gly Trp His Ser Trp Pro Ile Ala His Gln
                500                 505                 510
Trp Pro Gln Gly Pro Ser Ala Val Asp Ala Ala Phe Ser Trp Glu Glu
                515                 520                 525
Lys Leu Tyr Leu Val Gln Gly Thr Gln Val Tyr Val Phe Leu Thr Lys
                530                 535                 540
Gly Gly Tyr Thr Leu Val Ser Gly Tyr Pro Lys Arg Leu Glu Lys Glu
545                 550                 555                 560
Val Gly Thr Pro His Gly Ile Ile Leu Asp Ser Val Asp Ala Ala Phe
                565                 570                 575
Ile Cys Pro Gly Ser Ser Arg Leu His Ile Met Ala Gly Arg Arg Leu
                580                 585                 590
Trp Trp Leu Asp Leu Lys Ser Gly Ala Gln Ala Thr Trp Thr Glu Leu
                595                 600                 605
Pro Trp Pro His Glu Lys Val Asp Gly Ala Leu Cys Met Glu Lys Ser
610                 615                 620
Leu Gly Pro Asn Ser Cys Ser Ala Asn Gly Pro Gly Leu Tyr Leu Ile
625                 630                 635                 640
His Gly Pro Asn Leu Tyr Cys Tyr Ser Asp Val Glu Lys Leu Asn Ala
                645                 650                 655
Ala Lys Ala Leu Pro Gln Pro Gln Asn Val Thr Ser Leu Leu Gly Cys
                660                 665                 670
Thr His

<210> SEQ ID NO 4
<211> LENGTH: 468
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 4

```
Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
210                 215                 220

Thr Gln Lys Ser Leu Ser Leu Ser Pro Gly Ala Thr Pro Leu Pro Pro
225                 230                 235                 240

Thr Ser Ala His Gly Asn Val Ala Glu Gly Thr Lys Pro Asp Pro
                245                 250                 255

Asp Val Thr Glu Arg Cys Ser Asp Gly Trp Ser Phe Asp Ala Thr Thr
                260                 265                 270

Leu Asp Asp Asn Gly Thr Met Leu Phe Phe Lys Gly Glu Phe Val Trp
        275                 280                 285

Lys Ser His Lys Trp Asp Arg Glu Leu Ile Ser Glu Arg Trp Lys Asn
290                 295                 300

Phe Pro Ser Pro Val Asp Ala Ala Phe Arg Gln Gly His Asn Ser Val
305                 310                 315                 320

Phe Leu Ile Lys Gly Asp Lys Val Trp Val Tyr Pro Pro Glu Lys Lys
                325                 330                 335

Glu Lys Gly Tyr Pro Lys Leu Leu Gln Asp Glu Phe Pro Gly Ile Pro
            340                 345                 350

Ser Pro Leu Asp Ala Ala Val Glu Cys His Arg Gly Glu Cys Gln Ala
        355                 360                 365

Glu Gly Val Leu Phe Phe Gln Gly Asp Arg Glu Trp Phe Trp Asp Leu
370                 375                 380

Ala Thr Gly Thr Met Lys Glu Arg Ser Trp Pro Ala Val Gly Asn Cys
385                 390                 395                 400
```

```
Ser Ser Ala Leu Arg Trp Leu Gly Arg Tyr Tyr Cys Phe Gln Gly Asn
                405                 410                 415

Gln Phe Leu Arg Phe Asp Pro Val Arg Gly Glu Val Pro Pro Arg Tyr
            420                 425                 430

Pro Arg Asp Val Arg Asp Tyr Phe Met Pro Cys Pro Gly Arg Gly His
        435                 440                 445

Gly His Arg Asn Gly Thr Gly His Gly Asn Ser Thr His His Gly Pro
    450                 455                 460

Glu Tyr Met Arg
465

<210> SEQ ID NO 5
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asp Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala Thr Pro Leu Pro Pro Thr Ser Ala
225                 230                 235                 240

His Gly Asn Val Ala Glu Gly Glu Thr Lys Pro Asp Pro Asp Val Thr
                245                 250                 255

Glu Arg Cys Ser Asp Gly Trp Ser Phe Asp Ala Thr Thr Leu Asp Asp
            260                 265                 270

Asn Gly Thr Met Leu Phe Phe Lys Gly Glu Phe Val Trp Lys Ser His
```

```
                    275                 280                 285
        Lys Trp Asp Arg Glu Leu Ile Ser Glu Arg Trp Lys Asn Phe Pro Ser
            290                 295                 300
        Pro Val Asp Ala Ala Phe Arg Gln Gly His Asn Ser Val Phe Leu Ile
        305                 310                 315                 320
        Lys Gly Asp Lys Val Trp Val Tyr Pro Pro Glu Lys Lys Glu Lys Gly
                        325                 330                 335
        Tyr Pro Lys Leu Leu Gln Asp Glu Phe Pro Gly Ile Pro Ser Pro Leu
                    340                 345                 350
        Asp Ala Val Glu Cys His Arg Gly Glu Cys Gln Ala Glu Gly Val
                355                 360                 365
        Leu Phe Phe Gln Gly Asp Arg Glu Trp Phe Trp Asp Leu Ala Thr Gly
            370                 375                 380
        Thr Met Lys Glu Arg Ser Trp Pro Ala Val Gly Asn Cys Ser Ser Ala
        385                 390                 395                 400
        Leu Arg Trp Leu Gly Arg Tyr Tyr Cys Phe Gln Gly Asn Gln Phe Leu
                        405                 410                 415
        Arg Phe Asp Pro Val Arg Gly Glu Val Pro Pro Arg Tyr Pro Arg Asp
                    420                 425                 430
        Val Arg Asp Tyr Phe Met Pro Cys Pro Gly Arg Gly His Gly His Arg
                435                 440                 445
        Asn Gly Thr Gly His Gly Asn Ser Thr His His Gly Pro Glu Tyr Met
        450                 455                 460
        Arg
        465

<210> SEQ ID NO 6
<211> LENGTH: 1635
<212> TYPE: DNA
<213> ORGANISM: Homo sapiens

<400> SEQUENCE: 6
aactctatat agggagttca actggtcacc cagagctgtc ctgtggcctc tgcagctcag       60
catggctagg gtactgggag cacccgttgc actggggttg tggagcctat gctggtctct      120
ggccattgcc acccctcttc ctccgactag tgcccatggg aatgttgctg aaggcgagac      180
caagccagac ccagacgtga ctgaacgctg ctcagatggc tggagctttg atgctaccac      240
cctggatgac aatggaacca tgctgttttt taaagggggag tttgtgtgga agagtcacaa      300
atgggaccgg gagttaatct cagagagatg gaagaatttc cccagccctg tggatgctgc      360
attccgtcaa ggtcacaaca gtgtctttct gatcaagggg gacaaagtct gggtataccc      420
tcctgaaaag aaggagaaag atacccaaa gttgctccaa gatgaatttc ctggaatccc      480
atccccactg gatgcagctg tggaatgtca ccgtggagaa tgtcaagctg aaggcgtcct      540
cttcttccaa ggtgaccgcg agtggttctg ggacttggct acgggaacca tgaaggagcg      600
ttcctggcca gctgttggga actgctcctc tgccctgaga tggctgggcc gctactactg      660
cttccagggt aaccaattcc tgcgcttcga ccctgtcagg ggagaggtgc ctcccaggta      720
cccgcgggat gtccgagact acttcatgcc ctgcccctggc agaggccatg gacacaggaa      780
tgggactggc catgggaaca gtacccacca tggccctgag tatatgcgct gtagcccaca      840
tctagtcttg tctgcactga cgtctgacaa ccatggtgcc acctatgcct tcagtgggac      900
ccactactgg cgtctggaca ccagccggga tggctggcat agctggccca ttgctcatca      960
gtggccccag ggtccttcag cagtggatgc tgccttttcc tgggaagaaa aactctatct     1020
```

-continued

```
ggtccagggc acccaggtat atgtcttcct gacaaaggga ggctataccc tagtaagcgg    1080
ttatccgaag cggctggaga aggaagtcgg gacccctcat gggattatcc tggactctgt    1140
ggatgcggcc tttatctgcc ctgggtcttc tcggctccat atcatggcag acggcggct     1200 gtggtggctg gacctgaagt caggagccca agccacgtgg acagagcttc cttggcccca    1260
tgagaaggta gacggagcct tgtgtatgga aaagtccctt ggccctaact catgttccgc    1320
caatggtccc ggcttgtacc tcatccatgg tcccaatttg tactgctaca gtgatgtgga    1380
gaaactgaat gcagccaagg cccttccgca accccagaat gtgaccagtc tcctgggctg    1440
cactcactga ggggccttct gacatgagtc tggcctggcc ccacctccta gttcctcata    1500
ataaagacag attgcttctt cgcttctcac tgagggcct tctgacatga gtctggcctg     1560
gccccacctc cccagtttct cataataaag acagattgct tcttcacttg aatcaaggga    1620
cctaaaaaaa aaaaa                                                     1635
```

<210> SEQ ID NO 7
<211> LENGTH: 231
<212> TYPE: PRT
<213> ORGANISM: Homo sapiens

<400> SEQUENCE: 7

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asp Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230
```

<210> SEQ ID NO 8
<211> LENGTH: 231

<212> TYPE: PRT
<213> ORGANISM: Homo sapiens

<400> SEQUENCE: 8

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly
225                 230
```

<210> SEQ ID NO 9
<211> LENGTH: 233
<212> TYPE: PRT
<213> ORGANISM: Homo sapiens

<400> SEQUENCE: 9

```
Thr Pro Leu Pro Pro Thr Ser Ala His Gly Asn Val Ala Glu Gly Glu
1               5                   10                  15

Thr Lys Pro Asp Pro Asp Val Thr Glu Arg Cys Ser Asp Gly Trp Ser
            20                  25                  30

Phe Asp Ala Thr Thr Leu Asp Asp Asn Gly Thr Met Leu Phe Phe Lys
        35                  40                  45

Gly Glu Phe Val Trp Lys Ser His Lys Trp Asp Arg Glu Leu Ile Ser
    50                  55                  60

Glu Arg Trp Lys Asn Phe Pro Ser Pro Val Asp Ala Ala Phe Arg Gln
65                  70                  75                  80

Gly His Asn Ser Val Phe Leu Ile Lys Gly Asp Lys Val Trp Val Tyr
                85                  90                  95

Pro Pro Glu Lys Lys Glu Lys Gly Tyr Pro Lys Leu Leu Gln Asp Glu
            100                 105                 110
```

```
Phe Pro Gly Ile Pro Ser Pro Leu Asp Ala Ala Val Glu Cys His Arg
            115                 120                 125

Gly Glu Cys Gln Ala Glu Gly Val Leu Phe Phe Gln Gly Asp Arg Glu
130                 135                 140

Trp Phe Trp Asp Leu Ala Thr Gly Thr Met Lys Glu Arg Ser Trp Pro
145                 150                 155                 160

Ala Val Gly Asn Cys Ser Ser Ala Leu Arg Trp Leu Gly Arg Tyr Tyr
                165                 170                 175

Cys Phe Gln Gly Asn Gln Phe Leu Arg Phe Asp Pro Val Arg Gly Glu
                180                 185                 190

Val Pro Pro Arg Tyr Pro Arg Asp Val Arg Asp Tyr Phe Met Pro Cys
            195                 200                 205

Pro Gly Arg Gly His Gly His Arg Asn Gly Thr Gly His Gly Asn Ser
            210                 215                 220

Thr His His Gly Pro Glu Tyr Met Arg
225                 230

<210> SEQ ID NO 10
<211> LENGTH: 210
<212> TYPE: PRT
<213> ORGANISM: Homo sapiens

<400> SEQUENCE: 10

Thr Glu Arg Cys Ser Asp Gly Trp Ser Phe Asp Ala Thr Thr Leu Asp
1               5                   10                  15

Asp Asn Gly Thr Met Leu Phe Phe Lys Gly Glu Phe Val Trp Lys Ser
            20                  25                  30

His Lys Trp Asp Arg Glu Leu Ile Ser Glu Arg Trp Lys Asn Phe Pro
        35                  40                  45

Ser Pro Val Asp Ala Ala Phe Arg Gln Gly His Asn Ser Val Phe Leu
    50                  55                  60

Ile Lys Gly Asp Lys Val Trp Val Tyr Pro Pro Glu Lys Lys Glu Lys
65                  70                  75                  80

Gly Tyr Pro Lys Leu Leu Gln Asp Glu Phe Pro Gly Ile Pro Ser Pro
                85                  90                  95

Leu Asp Ala Ala Val Glu Cys His Arg Gly Glu Cys Gln Ala Glu Gly
            100                 105                 110

Val Leu Phe Phe Gln Gly Asp Arg Glu Trp Phe Trp Asp Leu Ala Thr
        115                 120                 125

Gly Thr Met Lys Glu Arg Ser Trp Pro Ala Val Gly Asn Cys Ser Ser
    130                 135                 140

Ala Leu Arg Trp Leu Gly Arg Tyr Tyr Cys Phe Gln Gly Asn Gln Phe
145                 150                 155                 160

Leu Arg Phe Asp Pro Val Arg Gly Glu Val Pro Pro Tyr Pro Arg
                165                 170                 175

Asp Val Arg Asp Tyr Phe Met Pro Cys Pro Gly Arg Gly His Gly His
            180                 185                 190

Arg Asn Gly Thr Gly His Gly Asn Ser Thr His His Gly Pro Glu Tyr
        195                 200                 205

Met Arg
    210

<210> SEQ ID NO 11
<211> LENGTH: 206
<212> TYPE: PRT
<213> ORGANISM: Homo sapiens
```

<400> SEQUENCE: 11

| Ser | Asp | Gly | Trp | Ser | Phe | Asp | Ala | Thr | Thr | Leu | Asp | Asp | Asn | Gly | Thr |
|---|---|---|---|---|---|---|---|---|---|---|---|---|---|---|---|
| 1 | | | | 5 | | | | | 10 | | | | | 15 | |

| Met | Leu | Phe | Phe | Lys | Gly | Glu | Phe | Val | Trp | Lys | Ser | His | Lys | Trp | Asp |
|---|---|---|---|---|---|---|---|---|---|---|---|---|---|---|---|
| | | | 20 | | | | | 25 | | | | | 30 | | |

| Arg | Glu | Leu | Ile | Ser | Glu | Arg | Trp | Lys | Asn | Phe | Pro | Ser | Pro | Val | Asp |
|---|---|---|---|---|---|---|---|---|---|---|---|---|---|---|---|
| | | | 35 | | | | | 40 | | | | | 45 | | |

| Ala | Ala | Phe | Arg | Gln | Gly | His | Asn | Ser | Val | Phe | Leu | Ile | Lys | Gly | Asp |
|---|---|---|---|---|---|---|---|---|---|---|---|---|---|---|---|
| | 50 | | | | | 55 | | | | | 60 | | | | |

| Lys | Val | Trp | Val | Tyr | Pro | Pro | Glu | Lys | Lys | Glu | Lys | Gly | Tyr | Pro | Lys |
|---|---|---|---|---|---|---|---|---|---|---|---|---|---|---|---|
| 65 | | | | | 70 | | | | | 75 | | | | | 80 |

| Leu | Leu | Gln | Asp | Glu | Phe | Pro | Gly | Ile | Pro | Ser | Pro | Leu | Asp | Ala | Ala |
|---|---|---|---|---|---|---|---|---|---|---|---|---|---|---|---|
| | | | | 85 | | | | | 90 | | | | | 95 | |

| Val | Glu | Cys | His | Arg | Gly | Glu | Cys | Gln | Ala | Glu | Gly | Val | Leu | Phe | Phe |
|---|---|---|---|---|---|---|---|---|---|---|---|---|---|---|---|
| | | | 100 | | | | | 105 | | | | | 110 | | |

| Gln | Gly | Asp | Arg | Glu | Trp | Phe | Trp | Asp | Leu | Ala | Thr | Gly | Thr | Met | Lys |
|---|---|---|---|---|---|---|---|---|---|---|---|---|---|---|---|
| | | | 115 | | | | | 120 | | | | | 125 | | |

| Glu | Arg | Ser | Trp | Pro | Ala | Val | Gly | Asn | Cys | Ser | Ser | Ala | Leu | Arg | Trp |
|---|---|---|---|---|---|---|---|---|---|---|---|---|---|---|---|
| | 130 | | | | | 135 | | | | | 140 | | | | |

| Leu | Gly | Arg | Tyr | Tyr | Cys | Phe | Gln | Gly | Asn | Gln | Phe | Leu | Arg | Phe | Asp |
|---|---|---|---|---|---|---|---|---|---|---|---|---|---|---|---|
| 145 | | | | | 150 | | | | | 155 | | | | | 160 |

| Pro | Val | Arg | Gly | Glu | Val | Pro | Pro | Arg | Tyr | Pro | Arg | Asp | Val | Arg | Asp |
|---|---|---|---|---|---|---|---|---|---|---|---|---|---|---|---|
| | | | | 165 | | | | | 170 | | | | | 175 | |

| Tyr | Phe | Met | Pro | Cys | Pro | Gly | Arg | Gly | His | Gly | His | Arg | Asn | Gly | Thr |
|---|---|---|---|---|---|---|---|---|---|---|---|---|---|---|---|
| | | | 180 | | | | | 185 | | | | | 190 | | |

| Gly | His | Gly | Asn | Ser | Thr | His | His | Gly | Pro | Glu | Tyr | Met | Arg |
|---|---|---|---|---|---|---|---|---|---|---|---|---|---|
| | | 195 | | | | | 200 | | | | | 205 | |

<210> SEQ ID NO 12
<211> LENGTH: 220
<212> TYPE: PRT
<213> ORGANISM: Homo sapiens

<400> SEQUENCE: 12

| Thr | Pro | Leu | Pro | Pro | Thr | Ser | Ala | His | Gly | Asn | Val | Ala | Glu | Gly | Glu |
|---|---|---|---|---|---|---|---|---|---|---|---|---|---|---|---|
| 1 | | | | 5 | | | | | 10 | | | | | 15 | |

| Thr | Lys | Pro | Asp | Pro | Asp | Val | Thr | Glu | Arg | Cys | Ser | Asp | Gly | Trp | Ser |
|---|---|---|---|---|---|---|---|---|---|---|---|---|---|---|---|
| | | | 20 | | | | | 25 | | | | | 30 | | |

| Phe | Asp | Ala | Thr | Thr | Leu | Asp | Asp | Asn | Gly | Thr | Met | Leu | Phe | Phe | Lys |
|---|---|---|---|---|---|---|---|---|---|---|---|---|---|---|---|
| | | | 35 | | | | | 40 | | | | | 45 | | |

| Gly | Glu | Phe | Val | Trp | Lys | Ser | His | Lys | Trp | Asp | Arg | Glu | Leu | Ile | Ser |
|---|---|---|---|---|---|---|---|---|---|---|---|---|---|---|---|
| | 50 | | | | | 55 | | | | | 60 | | | | |

| Glu | Arg | Trp | Lys | Asn | Phe | Pro | Ser | Pro | Val | Asp | Ala | Ala | Phe | Arg | Gln |
|---|---|---|---|---|---|---|---|---|---|---|---|---|---|---|---|
| 65 | | | | | 70 | | | | | 75 | | | | | 80 |

| Gly | His | Asn | Ser | Val | Phe | Leu | Ile | Lys | Gly | Asp | Lys | Val | Trp | Val | Tyr |
|---|---|---|---|---|---|---|---|---|---|---|---|---|---|---|---|
| | | | | 85 | | | | | 90 | | | | | 95 | |

| Pro | Pro | Glu | Lys | Lys | Glu | Lys | Gly | Tyr | Pro | Lys | Leu | Leu | Gln | Asp | Glu |
|---|---|---|---|---|---|---|---|---|---|---|---|---|---|---|---|
| | | | 100 | | | | | 105 | | | | | 110 | | |

| Phe | Pro | Gly | Ile | Pro | Ser | Pro | Leu | Asp | Ala | Ala | Val | Glu | Cys | His | Arg |
|---|---|---|---|---|---|---|---|---|---|---|---|---|---|---|---|
| | | | 115 | | | | | 120 | | | | | 125 | | |

| Gly | Glu | Cys | Gln | Ala | Glu | Gly | Val | Leu | Phe | Phe | Gln | Gly | Asp | Arg | Glu |
|---|---|---|---|---|---|---|---|---|---|---|---|---|---|---|---|
| | 130 | | | | | 135 | | | | | 140 | | | | |

| Trp | Phe | Trp | Asp | Leu | Ala | Thr | Gly | Thr | Met | Lys | Glu | Arg | Ser | Trp | Pro |
|---|---|---|---|---|---|---|---|---|---|---|---|---|---|---|---|
| 145 | | | | | 150 | | | | | 155 | | | | | 160 |

```
Ala Val Gly Asn Cys Ser Ser Ala Leu Arg Trp Leu Gly Arg Tyr Tyr
            165                 170                 175

Cys Phe Gln Gly Asn Gln Phe Leu Arg Phe Asp Pro Val Arg Gly Glu
        180                 185                 190

Val Pro Pro Arg Tyr Pro Arg Asp Val Arg Asp Tyr Phe Met Pro Cys
        195                 200                 205

Pro Gly Arg Gly His Gly His Arg Asn Gly Thr Gly
    210                 215                 220

<210> SEQ ID NO 13
<211> LENGTH: 213
<212> TYPE: PRT
<213> ORGANISM: Homo sapiens

<400> SEQUENCE: 13

Thr Pro Leu Pro Pro Thr Ser Ala His Gly Asn Val Ala Glu Gly Glu
1               5                   10                  15

Thr Lys Pro Asp Pro Asp Val Thr Glu Arg Cys Ser Asp Gly Trp Ser
            20                  25                  30

Phe Asp Ala Thr Thr Leu Asp Asp Asn Gly Thr Met Leu Phe Phe Lys
        35                  40                  45

Gly Glu Phe Val Trp Lys Ser His Lys Trp Asp Arg Glu Leu Ile Ser
    50                  55                  60

Glu Arg Trp Lys Asn Phe Pro Ser Pro Val Asp Ala Ala Phe Arg Gln
65                  70                  75                  80

Gly His Asn Ser Val Phe Leu Ile Lys Gly Asp Lys Val Trp Val Tyr
                85                  90                  95

Pro Pro Glu Lys Lys Glu Lys Gly Tyr Pro Lys Leu Leu Gln Asp Glu
            100                 105                 110

Phe Pro Gly Ile Pro Ser Pro Leu Asp Ala Ala Val Glu Cys His Arg
        115                 120                 125

Gly Glu Cys Gln Ala Glu Gly Val Leu Phe Phe Gln Gly Asp Arg Glu
    130                 135                 140

Trp Phe Trp Asp Leu Ala Thr Gly Thr Met Lys Glu Arg Ser Trp Pro
145                 150                 155                 160

Ala Val Gly Asn Cys Ser Ser Ala Leu Arg Trp Leu Gly Arg Tyr Tyr
                165                 170                 175

Cys Phe Gln Gly Asn Gln Phe Leu Arg Phe Asp Pro Val Arg Gly Glu
            180                 185                 190

Val Pro Pro Arg Tyr Pro Arg Asp Val Arg Asp Tyr Phe Met Pro Cys
        195                 200                 205

Pro Gly Arg Gly His
    210

<210> SEQ ID NO 14
<211> LENGTH: 212
<212> TYPE: PRT
<213> ORGANISM: Homo sapiens

<400> SEQUENCE: 14

Thr Pro Leu Pro Pro Thr Ser Ala His Gly Asn Val Ala Glu Gly Glu
1               5                   10                  15

Thr Lys Pro Asp Pro Asp Val Thr Glu Arg Cys Ser Asp Gly Trp Ser
            20                  25                  30

Phe Asp Ala Thr Thr Leu Asp Asp Asn Gly Thr Met Leu Phe Phe Lys
        35                  40                  45
```

Gly Glu Phe Val Trp Lys Ser His Lys Trp Asp Arg Glu Leu Ile Ser
            50                  55                  60

Glu Arg Trp Lys Asn Phe Pro Ser Pro Val Asp Ala Ala Phe Arg Gln
 65                  70                  75                  80

Gly His Asn Ser Val Phe Leu Ile Lys Gly Asp Lys Val Trp Val Tyr
                    85                  90                  95

Pro Pro Glu Lys Lys Glu Lys Gly Tyr Pro Lys Leu Leu Gln Asp Glu
                100                 105                 110

Phe Pro Gly Ile Pro Ser Pro Leu Asp Ala Ala Val Glu Cys His Arg
                115                 120                 125

Gly Glu Cys Gln Ala Glu Gly Val Leu Phe Phe Gln Gly Asp Arg Glu
        130                 135                 140

Trp Phe Trp Asp Leu Ala Thr Gly Thr Met Lys Glu Arg Ser Trp Pro
145                 150                 155                 160

Ala Val Gly Asn Cys Ser Ser Ala Leu Arg Trp Leu Gly Arg Tyr Tyr
                    165                 170                 175

Cys Phe Gln Gly Asn Gln Phe Leu Arg Phe Asp Pro Val Arg Gly Glu
                180                 185                 190

Val Pro Pro Arg Tyr Pro Arg Asp Val Arg Asp Tyr Phe Met Pro Cys
                195                 200                 205

Pro Gly Arg Gly
    210

<210> SEQ ID NO 15
<211> LENGTH: 207
<212> TYPE: PRT
<213> ORGANISM: Homo sapiens

<400> SEQUENCE: 15

Thr Pro Leu Pro Pro Thr Ser Ala His Gly Asn Val Ala Glu Gly Glu
 1               5                  10                  15

Thr Lys Pro Asp Pro Asp Val Thr Glu Arg Cys Ser Asp Gly Trp Ser
                 20                  25                  30

Phe Asp Ala Thr Thr Leu Asp Asp Asn Gly Thr Met Leu Phe Phe Lys
            35                  40                  45

Gly Glu Phe Val Trp Lys Ser His Lys Trp Asp Arg Glu Leu Ile Ser
            50                  55                  60

Glu Arg Trp Lys Asn Phe Pro Ser Pro Val Asp Ala Ala Phe Arg Gln
 65                  70                  75                  80

Gly His Asn Ser Val Phe Leu Ile Lys Gly Asp Lys Val Trp Val Tyr
                    85                  90                  95

Pro Pro Glu Lys Lys Glu Lys Gly Tyr Pro Lys Leu Leu Gln Asp Glu
                100                 105                 110

Phe Pro Gly Ile Pro Ser Pro Leu Asp Ala Ala Val Glu Cys His Arg
                115                 120                 125

Gly Glu Cys Gln Ala Glu Gly Val Leu Phe Phe Gln Gly Asp Arg Glu
        130                 135                 140

Trp Phe Trp Asp Leu Ala Thr Gly Thr Met Lys Glu Arg Ser Trp Pro
145                 150                 155                 160

Ala Val Gly Asn Cys Ser Ser Ala Leu Arg Trp Leu Gly Arg Tyr Tyr
                    165                 170                 175

Cys Phe Gln Gly Asn Gln Phe Leu Arg Phe Asp Pro Val Arg Gly Glu
                180                 185                 190

Val Pro Pro Arg Tyr Pro Arg Asp Val Arg Asp Tyr Phe Met Pro 195                 200                 205

<210> SEQ ID NO 16
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Thr Pro Leu Pro Pro Thr Ser Ala His Gly Asn Val Ala Glu Gly Glu
1               5                   10                  15

Thr Lys Pro Asp Pro Asp Val Thr Glu Arg Cys Ser Asp Gly Trp Ser
            20                  25                  30

Phe Asp Ala Thr Thr Leu Asp Asp Asn Gly Thr Met Leu Phe Phe Lys
        35                  40                  45

Gly Glu Phe Val Trp Lys Ser His Lys Trp Asp Arg Glu Leu Ile Ser
    50                  55                  60

Glu Arg Trp Lys Asn Phe Pro Ser Pro Val Asp Ala Ala Phe Arg Gln
65                  70                  75                  80

Gly His Asn Ser Val Phe Leu Ile Lys Gly Asp Lys Val Trp Val Tyr
                85                  90                  95

Pro Pro Glu Lys Lys Glu Lys Gly Tyr Pro Lys Leu Leu Gln Asp Glu
            100                 105                 110

Phe Pro Gly Ile Pro Ser Pro Leu Asp Ala Ala Val Glu Cys His Arg
        115                 120                 125

Gly Glu Cys Gln Ala Glu Gly Val Leu Phe Phe Gln Gly Asp Arg Glu
    130                 135                 140

Trp Phe Trp Asp Leu Ala Thr Gly Thr Met Lys Glu Arg Ser Trp Pro
145                 150                 155                 160

Ala Val Gly Asn Cys Ser Ser Ala Leu Arg Trp Leu Gly Arg Tyr Tyr
                165                 170                 175

Cys Phe Gln Gly Asn Gln Phe Leu Arg Phe Asp Pro Val Arg Gly Glu
            180                 185                 190

Val Pro Pro Arg Tyr Pro Arg Asp Val Arg Asp Tyr Phe Met Pro Cys
        195                 200                 205

Pro Gly Arg Gly His Gly His Arg Asn Gly Thr Gly Ser Gly Ser His
    210                 215                 220

His Gly Pro Glu Tyr Met Arg Cys Ser Pro His Leu Val Leu Ser Ala
225                 230                 235                 240

Leu Thr Ser Asp Asn His Gly Ala Thr Tyr Ala Phe Ser Gly Thr His
                245                 250                 255

Tyr Trp Arg Leu Asp Thr Ser Arg Asp Gly Trp His Ser Trp Pro Ile
            260                 265                 270

Ala His Gln Trp Pro Gln Gly Pro Ser Ala Val Asp Ala Ala Phe Ser
        275                 280                 285

Trp Glu Glu Lys Leu Tyr Leu Val Gln Gly Thr Gln Val Tyr Val Phe
    290                 295                 300

Leu Thr Lys Gly Gly Tyr Thr Leu Val Ser Gly Tyr Pro Lys Arg Leu
305                 310                 315                 320

Glu Lys Glu Val Gly Thr Pro His Gly Ile Ile Leu Asp Ser Val Asp
                325                 330                 335

Ala Ala Phe Ile Cys Pro Gly Ser Ser Arg Leu His Ile Met Ala Gly
            340                 345                 350

Arg Arg Leu Trp Trp Leu Asp Leu Lys Ser Gly Ala Gln Ala Thr Trp
            355                 360                 365

Thr Glu Leu Pro Trp Pro His Glu Lys Val Asp Gly Ala Leu Cys Met
    370                 375                 380

Glu Lys Ser Leu Gly Pro Asn Ser Cys Ser Ala Asn Gly Pro Gly Leu
385                 390                 395                 400

Tyr Leu Ile His Gly Pro Asn Leu Tyr Cys Tyr Ser Asp Val Glu Lys
                405                 410                 415

Leu Asn Ala Ala Lys Ala Leu Pro Gln Pro Gln Asn Val Thr Ser Leu
            420                 425                 430

Leu Gly Cys Thr His
            435

<210> SEQ ID NO 17
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asp Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Ala
225                 230                 235

<210> SEQ ID NO 18
<211> LENGTH: 4
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 18

Gly Ser Gly Ser
1

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Pro Gly Gln Gly Leu Arg Gly Leu Gln Gly Pro Pro Gly Lys Leu
1               5                   10                  15

Gly Pro Pro Gly Asn Pro Gly Pro Ser Gly Ser
            20                  25

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Lys Leu Gly
1

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Pro Pro Gly Lys Leu Gly Pro Pro Gly Asn
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Gly Leu Gln Gly Pro Pro Gly Lys Leu
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23
```

```
Gly Lys Leu Gly Pro Pro Gly Asn Pro Gly Pro Ser Gly Ser
1               5                   10
```

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Gly Leu Arg Gly Leu Gln Gly Pro Pro Gly Lys Leu Gly Pro Pro Gly
1               5                   10                  15

Asn Pro Gly Pro
            20
```

<210> SEQ ID NO 25
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Pro Asp Gly Asp Ser Ser Leu Ala Ala Ser Glu Arg Lys Ala Leu Gln
1               5                   10                  15

Thr Glu Met Ala Arg Ile Lys Lys Trp Leu Thr Phe Ser Leu Gly Lys
                20                  25                  30

Gln
```

<210> SEQ ID NO 26
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Ala Pro Asp Gly Asp Ser Ser Leu Ala Ala Ser Glu Arg Lys Ala Leu
1               5                   10                  15

Gln Thr Glu Met Ala Arg Ile Lys Lys Trp Leu Thr Phe Ser Leu Gly
                20                  25                  30

Lys Gln
```

<210> SEQ ID NO 27
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Pro Asp Gly Asp Ser Ser Leu Ala Ala Ser Glu Arg Lys Ala Leu Gln
1               5                   10                  15

Thr Glu Met Ala Arg Ile Lys Lys Trp Leu Thr Phe Ser Leu Gly
                20                  25                  30
```

<210> SEQ ID NO 28
<211> LENGTH: 32
<212> TYPE: PRT

<213> ORGANISM: Artificial Sequence
<220> FEATURE:
<223> OTHER INFORMATION: Description of Artificial Sequence: Synthetic
     polypeptide

<400> SEQUENCE: 28

Ala Pro Asp Gly Asp Ser Ser Leu Ala Ala Ser Glu Arg Lys Ala Leu
1               5                   10                  15
Gln Thr Glu Met Ala Arg Ile Lys Lys Trp Leu Thr Phe Ser Leu Gly
            20                  25                  30

<210> SEQ ID NO 29
<211> LENGTH: 2
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 29

Asn Asp
1

<210> SEQ ID NO 30
<211> LENGTH: 3
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<221> NAME/KEY: MOD_RES
<222> LOCATION: (2)..(2)
<223> OTHER INFORMATION: Any amino acid

<400> SEQUENCE: 30

Glu Xaa Asn
1

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 31

Asn Glu Gly Glu Pro Asn Asn Ala Gly Ser
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 32

Gly Ser Asp Glu Asp Cys Val Leu Leu
1               5

<210> SEQ ID NO 33
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 33

Leu Leu Leu Lys Asn Gly Gln Trp Asn Asp Val Pro Cys Ser Thr
1               5                   10                  15

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 34

His His His His His His
1               5

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Lys Thr
1
```

ENGINEERED HEME-BINDING COMPOSITIONS AND USES THEREOF

CROSS-REFERENCE TO RELATED APPLICATIONS

This application is a continuation under 35 U.S.C. § 120 of U.S. application Ser. No. 15/968,116 filed May 1, 2018, which issued as U.S. Pat. No. 10,501,729 on Dec. 10, 2019, which is a continuation under 35 U.S.C. § 120 of U.S. application Ser. No. 14/892,252 filed Nov. 19, 2015, which issued as U.S. Pat. No. 9,988,617 on Jun. 5, 2018, which is a 35 U.S.C. § 371 National Phase Entry Application of International Application No. PCT/US2014/038945 filed May 21, 2014, which designates the U.S., and which claims benefit under 35 U.S.C. § 119(e) of U.S. Provisional Application No. 61/825,707 filed May 21, 2013, the contents of which are incorporated herein by reference in their entireties.

GOVERNMENT SUPPORT

This invention was made with government support under Grant Nos. N66001-11-1-4180 awarded by the U.S. Department of Defense. The government has certain rights in the invention.

SEQUENCE LISTING

The instant application contains a Sequence Listing which has been submitted electronically in ASCII format and is hereby incorporated by reference in its entirety. Said ASCII copy, created on Nov. 18, 2015, is named 002806-076882-US_SL.txt and is 51,193 bytes in size.

TECHNICAL FIELD

The technology described herein relates to methods and compositions relating to the treatment of heme and/or myoglobin-associated disease and disorders, e.g. sepsis, rhabdomyolysis, crush injury, and the like.

BACKGROUND

Sepsis is a lethal condition that is often associated with a serious microbial infection. However, while many hypotheses have been put forward, the exact cause of septic shock is not agreed upon and therapeutics based on targeting the source of these various hypotheses have generally failed in (or prior to) clinical trials. The current treatment generally includes administration of antibiotics. Past clinical trials have focused on limiting the immune systems response to microbial infections, thereby reducing the "Cytokine Storm" that has been hypothesized to be the causative agent of sepsis. In addition, people have looked to use dialysis to remove cytokines.

SUMMARY

Described herein are methods and compositions relating to the treatment of heme and/or myoglobin-associated disease and disorders, e.g. sepsis and rhabdomyolysis. The technology described herein is based upon the recognition that excess free heme in the blood can play a role in the progression of sepsis. In a septic patient or animal, microbial infections can lead to a large increase in Red Blood Cell (RBS) lysis, which in turn leads to a significant increase in soluble free heme in the blood stream. This increase overwhelms the endogenous levels of hemopexin, which normally scavenges endogenous levels of heme, leading to dangerously high levels of heme. Excess heme in the blood provides microbial pathogens with a readily available source of iron, which can be limiting agent in microbial growth and hemoglobin and heme may substantially contribute to microbe-induced inflammation when bacterial or viral infection coexists with blood.

As demonstrated herein, hemopexin fusion proteins can be used to lower the level of free heme in the blood of a subject, e.g. to treat sepsis. In one aspect, described herein is a heme-binding molecule and/or composition comprising a hemopexin domain conjugated to a Fc domain. In some embodiments, the hemopexin domain is a polypeptide comprising the sequence of SEQ ID NO: 2. In some embodiments, the hemopexin domain is a polypeptide having the sequence of SEQ ID NO: 2. In some embodiments, the composition has the sequence of SEQ ID NO: 4 or SEQ ID NO: 5.

In one aspect, described herein is a method of reducing the level of free heme in the blood of a subject, the method comprising contacting the blood of the subject with a heme-binding molecule and/or composition described herein. In some embodiments, the method further comprises removing a portion of the subject's blood prior to the contacting step and performing the contacting step extracorporeally and then returning the portion of the subject's blood to the subject. In some embodiments, the heme-binding molecule and/or composition is bound to a solid substrate of an extracorporeal device. In some embodiments, the solid substrate is a filter or affinity column. In some embodiments, the heme-binding molecule and/or composition can be administered to a subject as a therapeutic agent.

In one aspect, described herein is a method of producing a heme-binding molecule and/or composition, the method comprising culturing a cell comprising a nucleic acid encoding a heme-binding molecule and/or composition described herein under conditions suitable for the production of proteins and purifying the heme-binding molecule and/or composition by affinity purification with a stabilization domain binding reagent. In some embodiments, the cell is a microbial cell or a mammalian cell.

DETAILED DESCRIPTION

Figure 1:
FIG. 1 depicts an image of an SDS gel showing the purity of isolated Fc-Hemopexin fusions.

As described herein, the inventors have discovered that certain hemopexin fusion proteins can be used to binding free heme in blood. Accordingly, provided herein are methods and compositions relating to these fusion proteins and their use for reducing heme levels in the blood, e.g. for the treatment of sepsis.

In one aspect, the invention described herein relates to a heme-binding molecule and/or composition comprising a hemopexin domain conjugated to a Fc domain. In some embodiments, the composition can be a multimer. As used herein, "hemopexin domain" refers to a domain or portion of a polypeptide composition described herein comprising a hemopexin polypeptide or a fragment thereof "Hemopexin" (also referred to as "haemopexin," "HPX," or "beta-1B-glycoprotein" refers to a protein with the highest known affinity for heme and which interacts with the LRP1 receptor when complexed with heme. The sequences of hemopexin for a variety of species are known, e.g. human hemopexin (NCBI Gene ID: 3263 (SEQ ID NO: 1; NCBI Ref Seq: NP_00604; polypeptide)(SEQ ID NO: 6; NCBI Ref Seq: NM_000613; mRNA).

A hemopexin polypeptide can comprise SEQ ID NO: 1 or a homolog, variant, and/or functional fragment thereof. In some embodiments, a hemopexin polypeptide can comprise amino acids 24 to 462 of SEQ ID NO: 1 (i.e. the mature hemopexin polypeptide with the signal peptide sequence removed), or a homolog, variant, and/or functional fragment thereof. In some embodiments, a hemopexin domain can comprise amino acid 24 to amino acid 256 of SEQ ID NO: 1 or a homolog, variant, and/or functional fragment thereof. In some embodiments, a hemopexin domain can comprise amino acid 27 to amino acid 213 of SEQ ID NO: 1 or a homolog, variant, and/or functional fragment thereof. In some embodiments, a hemopexin domain can comprise amino acid 1 to amino acid 213, 220, 233, or 256 of SEQ ID NO: 1 or a homolog, variant, and/or functional fragment thereof. In some embodiments, a hemopexin domain can comprise amino acid 24 to amino acid 213, 220, 233, or 256 of SEQ ID NO: 1 or a homolog, variant, and/or functional fragment thereof. In some embodiments, a hemopexin domain can comprise amino acid 27 to amino acid 213, 220, 233, or 256 of SEQ ID NO: 1 or a homolog, variant, and/or functional fragment thereof. In some embodiments, a hemopexin polypeptide as described herein can be a homolog, derivative, variant, conservative substitution variant, deletion mutant, insertion mutant, or functional fragment of the amino acid sequences described above herein. In some embodiments, a hemopexin domain can comprise a mutation wherein the residues corresponding to residues 220-226 of SEQ ID NO: 1 have been replaced with the sequence GSGS (SEQ ID NO: 18).

In some embodiments, a hemopexin domain can comprise amino acid 24 to amino acid 256 of SEQ ID NO: 2 or a homolog, variant, and/or functional fragment thereof. In some embodiments, a hemopexin domain can comprise amino acid 27 to amino acid 213 of SEQ ID NO: 2 or a homolog, variant, and/or functional fragment thereof. In some embodiments, a hemopexin domain can comprise amino acid 1 to amino acid 213, 220, 233, or 256 of SEQ ID NO: 2 or a homolog, variant, and/or functional fragment thereof. In some embodiments, a hemopexin domain can comprise amino acid 24 to amino acid 213, 220, 233, or 256 of SEQ ID NO: 2 or a homolog, variant, and/or functional fragment thereof. In some embodiments, a hemopexin domain can comprise amino acid 27 to amino acid 213, 220, 233, or 256 of SEQ ID NO: 2 or a homolog, variant, and/or functional fragment thereof. In some embodiments, a hemopexin polypeptide as described herein can be a homolog, derivative, variant, conservative substitution variant, deletion mutant, insertion mutant, or functional fragment of the amino acid sequences described above herein. In some embodiments, a hemopexin domain can comprise a mutation wherein the residues corresponding to residues 220-226 of SEQ ID NO: 2 have been replaced with the sequence GSGS (SEQ ID NO: 18).

As used herein, a "functional fragment" of, e.g. SEQ ID NO: 1 is a fragment or segment of that polypeptide which can bind heme at least 10% as strongly as the reference polypeptide (i.e. SEQ ID NO: 1), e.g. at least 10%, at least 20%, at least 30%, at least 40%, at least 50%, at least 75%, at least 90%, at least 100% as strongly, or more strongly. Assays for determining heme concentrations and binding of a protein to heme are well known in the art and include, by way of non-limiting example, spectroscopic titrations using dithionite, e.g. as described in Airola et al. Biochemistry 2001 49:43217-4338; the assay described in U.S. Pat. No. 4,340,668; or any of the assays described in Sinclair et al. Current Protocols in Toxicology 2001; unit 8.3. Each of the foregoing references is incorporated by reference herein in its entirety. A functional fragment can comprise conservative substitutions of the sequences disclosed herein. In some embodiments, heme binding can include myoglobin binding activity.

Variants of the isolated peptides described herein (e.g. SEQ ID NOs: 1-5) can be obtained by mutations of native nucleotide or amino acid sequences, for example SEQ ID NO: 1 or a nucleotide sequence encoding a peptide comprising SEQ ID NO:1. A "variant," as referred to herein, is a polypeptide substantially homologous to an hemopexin polypeptide described herein (e.g. SEQ ID NOs: 1 and 2), but which has an amino acid sequence different from that of one of the sequences described herein because of one or a plurality of deletions, insertions or substitutions.

A homolog of a hemopexin polypeptide as described herein can also comprise amino acid sequences that are homologous to the regions of hemopexin comprised by the hemopexin polypeptide described herein.

The variant amino acid or DNA sequence preferably is at least 60%, at least 70%, at least 80%, at least 90%, at least 91%, at least 92%, at least 93%, at least 94%, at least 95%, at least 96%, at least 97%, at least 98%, at least 99%, or more, identical to the sequence from which it is derived (referred to herein as an "original" sequence). The degree of homology (percent identity) between an original and a mutant sequence can be determined, for example, by comparing the two sequences using freely available computer programs commonly employed for this purpose on the world wide web. The variant amino acid or DNA sequence preferably is at least 60%, at least 70%, at least 80%, at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp (available on the world wide web at http://blast.ncbi.nlm.nih.gov).

Alterations of the original amino acid sequence can be accomplished by any of a number of known techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. In some embodiments, an isolated peptide as described herein can be chemically synthesized and mutations can be incorporated as part of the chemical synthesis process.

Variants can comprise conservatively substituted sequences, meaning that one or more amino acid residues of an original peptide are replaced by different residues, and that the conservatively substituted peptide retains a desired biological activity, i.e., the ability to bind heme, that is essentially equivalent to that of the original peptide. Examples of conservative substitutions include substitutions that do not change the overall or local hydrophobic character, substitutions that do not change the overall or local charge, substitutions by residues of equivalent sidechain size, or substitutions by sidechains with similar reactive groups.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics or substitutions of residues with similar sidechain volume are well known. Isolated peptides comprising conservative amino acid substitutions can be tested in any one of the assays described herein to confirm that a desired activity, e.g. the ability to bind heme, is retained, as determined by the assays described elsewhere herein.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile, Phe, Trp; (2) neutral hydrophilic: Cys, Ser, Thr, Asn, Gln, Ala, Tyr, His, Pro, Gly; (3) acidic: Asp, Glu; (4) basic: His, Lys, Arg; (5) residues that influence chain orientation: Gly, Pro; (6) aromatic: Trp, Tyr, Phe, Pro, His, or hydroxyproline. Non-conservative substitutions will entail exchanging a member of one of these classes for another class.

Particularly preferred conservative substitutions for use in the variants described herein are as follows: Ala into Gly or into Ser; Arg into Lys; Asn into Gln or into His; Asp into Glu or into Asn; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr or into Phe; Tyr into Phe or into Trp; and/or Phe into Val, into Tyr, into Ile or into Leu. In general, conservative substitutions encompass residue exchanges with those of similar physicochemical properties (i.e. substitution of a hydrophobic residue for another hydrophobic amino acid).

Any cysteine residue not involved in maintaining the proper conformation of the isolated peptide as described herein can also be substituted, generally with serine, to improve the oxidative stability of the molecule and prevent aberrant crosslinking. Conversely, cysteine bond(s) can be added to the isolated peptide as described herein to improve its stability or facilitate multimerization.

In some embodiments, a functional fragment of hemopexin can comprise from about amino acid 24 to about amino acid 256 of SEQ ID NO: 1. In some embodiments, a functional fragment of hemopexin comprise amino acid 24 to amino acid 256 of SEQ ID NO: 1, i.e. SEQ ID NO: 2. In some embodiments, a functional fragment of hemopexin can be a polypeptide having the sequence of SEQ ID NO: 2.

As used herein, "a Fc domain" refers to domain, part, or portion of a polypeptide comprising an Fc polypeptide. As used herein, a "Fc polypeptide" refers to the region of an antibody that interacts with Fc receptors and certain components of the complement system. The Fc region for a given type of antibody will be constant for all antibodies of that type in an individual, whereas the Fab region of the antibody will vary, providing antigen specificity. In some embodiments, a Fc polypeptide can be a polypeptide having the sequence of SEQ ID NO: 7 or a or a homolog, variant, and/or functional fragment thereof. In some embodiments, a Fc polypeptide can be a polypeptide having the sequence of SEQ ID NO: 8 or a or a homolog, variant, and/or functional fragment thereof. In some embodiments, a Fc polypeptide can be a polypeptide having the sequence of SEQ ID NO: 17 or a or a homolog, variant, and/or functional fragment thereof. In the context of a FC polypeptide, a functional fragment is a fragment or segment of that polypeptide which can bind or be bound by Fc receptors and/or C1q at least 10% as strongly as the reference polypeptide (i.e. SEQ ID NO: 7), e.g. at least 10%, at least 20%, at least 30%, at least 40%, at least 50%, at least 75%, at least 90%, at least 100% as strongly, or more strongly. Assays for the binding of a ligand and its receptor are well known in the art.

In such embodiments, the Fc region can comprise at least one region selected from the group consisting of a hinge region, a CH2 region, a CH3 region, and any combinations thereof. By way of example, in some embodiments, a CH2 region can be excluded from the portion of the Fc region as the second domain. In one embodiment, Fc region comprised comprises a hinge region, a CH2 domain and a CH3 domain.

In some embodiments, the Fc region can be can be used to facilitate expression and purification of the engineered molecules and compositions described herein. The N terminal Fc has been shown to improve expression levels, protein folding and secretion of the fusion partner. In addition, the Fc has a staphylococcal Protein A binding site, which can be used for one-step purification protein A affinity chromatography. See Lo K M et al. (1998) Protein Eng. 11: 495-500. Further, the Protein A binding site can be used to facilitate binding of Protein A-expressing or Protein G-expressing microbes in the absence of calcium ions. Further, such Fc regions have a molecule weight above a renal threshold of about 45 kDa, thus reducing the possibility of engineered molecules being removed by glomerular filtration. Additionally, the Fc region can allow dimerization of two engineered heme-binding domain molecules to form a multimeric complex, such as a dimer.

In some embodiments, an Fc region or a fragment thereof can comprise at least one mutation, e.g., to modify the performance of the engineered heme-binding molecules and/or compositions. For example, in some embodiments, a half-life of the engineered heme-binding molecules and/or compositions described herein can be increased, e.g., by mutating an amino acid lysine (K) at the residue 224 of SEQ ID NO: 5 to alanine (A). Other mutations, e.g., located at the interface between the CH2 and CH3 domains shown in Hinton et al (2004) *J Biol Chem.* 279:6213-6216 and Vaccaro C. et al. (2005) *Nat Biotechnol.* 23: 1283-1288, can be also used to increase the half-life of the IgG1 and thus the engineered heme-binding molecules and/or compositions.

In some embodiments, the Fc polypeptide can comprise a N297D mutation, which results in an aglycosylated Fc polypeptide.

In some embodiments, the Fc polypeptide is a polypeptide that can be bound by an Fc receptor and internalized into a cell, e.g. into subcellular compartments. This can remove the bound heme from the blood and direct it into cellular recycling pathways. The Heme-Hemopexin complex is typically removed form the blood stream by CD91 mediated endocytosis. The Fc-Hemopexin molecule can increase this clearance rate by taking advantage of endocytosis and recycling of Fc containing proteins via its interaction with Fc receptors.

In one aspect, described herein is an engineered heme-binding molecule comprising a hemopexin domain and a linker, substrate-binding domain, and/or microbe-binding molecule conjugated thereto. As used herein, "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. For example, in some embodiments of the present invention, an engineered molecule comprises multiple domains that are each found in nature, but are not found in the same transcript in nature. As is common practice and is understood by those in the art, progeny and copies of an engineered polynucleotide are typically still referred to as "engineered" even though the actual manipulation was performed on a prior entity.

Multiple domains of the heme-binding composition and/or molecule can be linked together by a linker. Further, the heme-binding composition and/or molecule can be conjugated to a carrier scaffold via linker. Accordingly, as used in this disclosure, the term "linker" means a moiety that connects two parts of a compound or molecule. Linkers typically comprise a direct bond or an atom such as oxygen or sulfur, a unit such as $NR^1$, $C(O)$, $C(O)O$, $OC(O)O$, $C(O)NH$, $NHC(O)O$, $NH$, $SS$, $SO$, $SO_2$, $SO_3$, and $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, NH, $C(O)N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic. In some embodiments, the linker can be a non-covalent association (e.g., by non-covalent interactins) of the two parts of a molecule being conjugated together. Some exemplary non-covalent on ionic interactions, van der Waals interactions, dipole-dipole interactions, hydrogen bonds, electrostatic interactions, and/or shape recognition interactions.

In some embodiments, the linker can comprise at least one cleavable linking group. A cleavable linking group is one which is sufficiently stable under one set of conditions, but which is cleaved under a different set of conditions to release the two parts the linker is holding together. In some embodiments, the cleavable linking group is cleaved at least 10 times or more, e.g., at least 100 times faster under a first reference condition (which can, e.g., be selected to mimic or represent a microbe-infected condition, such as a microbe-infected tissue or body fluid, or a microbial biofilm occurring in an environment) than under a second reference condition (which can, e.g., be selected to mimic or represent non-infected conditions, e.g., found in the non-infected blood or serum, or in an non-infected environment).

Cleavable linking groups are susceptible to cleavage agents, e.g., hydrolysis, pH, redox potential or the presence of degradative molecules. Generally, cleavage agents are more prevalent or found at higher levels or activities at a site of interest (e.g. a microbial infection) than in non-infected area. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell, organ, or tissue to be targeted. In some embodiments, cleavable linking group is cleaved at least 1.25, 1.5, 1.75, 2, 3, 4, 5, 10, 25, 50, or 100 times faster under a first reference condition (or under in vitro conditions selected to mimic a microbe-infected condition, such as a microbe-infected tissue or body fluid, or a microbial biofilm occurring in an environment or on a working surface) than under a second reference condition (or under in vitro conditions selected to mimic non-infected conditions, e.g., found in the non-infected blood or serum, or in an non-infected environment). In some embodiments, the cleavable linking group is cleaved by less than 90%, 80%, 70%, 60%, 50%, 40%, 30%, 20%, 10%, 5%, or 1% in the non-infected conditions, e.g., found in the non-infected blood or serum, or in an non-infected environment, as compared to a microbe-infected condition, such as a microbe-infected tissue or body fluid, or a microbial biofilm occurring in an environment or on a working surface.

Exemplary cleavable linking groups include, but are not limited to, hydrolyzable linkers, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)

(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid celavable linking groups (e.g., hydrazones, esters, and esters of amino acids, —C≡NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease. In some embodiments, an acid cleavable linking group is cleavable in an acidic environment with a pH of about 6.5 or lower (e.g., about 6.5, 6.0, 5.5, 5.0, or lower), or by agents such as enzymes that can act as a general acid.

Without limitations, the linker can be selected to provide a desired function or property to the heme-binding molecules and/or compositions disclosed herein. For example, the linker can be selected or configured according to a specific need or use of the heme-binding molecules and/or compositions. By way of example only, in some embodiments, linker can be selected or configured to have a sufficient length and flexibility such that it can allow for the microbe-binding domain to orient in a desired orientation with respect to a microbe. In some embodiments, the linker can be selected or configured to allow multimerization of at least two engineered heme-binding molecules and/or compositions (e.g., to from a di-, tri-, tetra-, penta-, hexa- or higher multimeric complex) while retaining biological activity (e.g., heme-binding activity). In some embodiments, the linker can be selected or configured to inteact with a second domain (e.g. an Fc domain) to allow multimerization of at least two engineered heme-binding molecules and/or compositions (e.g., to from a di-, tri-, tetra-, penta-, hexa- or higher multimeric complex) while retaining heme-binding activity.

In some embodiments, the linker can be selected or configured to facilitate expression and purification of the engineered heme-binding molecules and/or compositions described herein. In some embodiments, the linker can be selected or configured to provide a recognition site for a protease or a nuclease. In addition, the linker can be nonreactive with the functional components of the engineered molecule described herein. For example, minimal hydrophobic or charged character to react with a domain of the heme-binding molecule and/or composition. In some embodiments, the linker can be part of a domain of the heme-binding molecule and/or composition.

In some embodiments, the linker can be a peptide or a nucleic acid. In some embodiments, the peptide linker can vary from about 1 to about 1000 amino acids long, from about 10 to about 500 amino acids long, from about 30 to about 300 amino acids long, or from about 50 to about 150 amino acids long. In some embodiments, the peptidyl linker is from about 1 amino acid to about 20 amino acids long. In some embodiments, the nucleic acid linker can vary from about 1 to about 1000 nucleotides long, from about 10 to about 500 nucleotides long, from about 30 to about 300 nucleotides, or from about 50 to about 150 nucleotides. Longer or shorter linker sequences can be also used for the engineered heme-binding molecules and/or compositions described herein.

The peptidyl linker can be configured to have a sequence comprising at least one of the amino acids selected from the group consisting of glycine (Gly), serine (Ser), asparagine (Asn), threonine (Thr), methionine (Met) or alanine (Ala). Such amino acids are generally used to provide flexibility of a linker. However, in some embodiments, other uncharged polar amino acids (e.g., Gln, Cys or Tyr), nonpolar amino acids (e.g., Val, Leu, Ile, Pro, Phe, and Trp). In alternative embodiments, polar amino acids can be added to modulate the flexibility of a linker. One of skill in the art can control flexibility of a linker by varying the types and numbers of residues in the linker. See, e.g., Perham, 30 Biochem. 8501 (1991); Wriggers et al., 80 Biopolymers 736 (2005).

In some embodiments, the peptidyl linker can comprise form 1 to about 25 amino acids, i.e., one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five amino acids. In some embodiments, the peptidyl linker linking the first and second domain comprises the amino acid sequence HHHHHH (SEQ ID NO: 34).

In some embodiments, when the heme-binding molecules and/or compositions comprise an Fc region, the linker linking the heme binding and the Fc domain is not a bond or a peptide.

In some embodiments, the linker is a bond.

In some embodiments, the linker conjugating a heme-binding molecule and/or composition to a carrier scaffold is a polyethylene glycol. Exemplary PEGs for use as linkers include, but are not limited to, PEG-2K, PEG-5K, PEG-10K, PEG-12K, PEG-15K, PEG-20K, PEG-40K, and the like.

In some embodiments, the linker can be albumin, transferrin or a fragment thereof. Without limitations, such linkers can be used to extend the plasma half-life of the engineered heme-binding molecules and/or compositions. Thus, engineered heme-binding molecules and/or compositions can be useful for in vivo administration. See Schmidt S R (2009) Curr Opin Drug Discov Devel. 12: 284. In some embodiments, the linker can be a physical substrate, e.g., microparticles or magnetic microbes.

A linker between a first domain and a second domain can provide sufficient distance between the first and the second domain to allow the first domain to interact with heme. Accordingly, in some embodiments, the distance between the first domain and the second domain can range from about 50 angstroms to about 5000 angstroms, from about 100 angstroms to about 2500 angstroms, or from about 200 angstroms to about 1000 angstroms.

The linkers can be of any shape. For example, the linker can be linear, folded, branched. In some embodiments, the linker can adopt the shape of a carrier scaffold. In some embodiments, the linkers can be linear. In some embodiments, the linkers can be folded. In some embodiments, the linkers can be branched. For branched linkers, each branch of a molecule can comprise at least one heme-binding domain. In other embodiments, the linker adopts the shape of the physical substrate.

In some embodiments, the heme-binding molecules and/or compositions can comprise a functional group for conjugating the hemopexin domain to another molecule, a composition, a physical substrate, and the like. For example, a second domain can comprise a functional group for covalently linking the heme-binding domain with another molecule molecule, a composition, a physical substrate, or the like. Some exemplary functional groups for conjugation include, but are not limited to, an amino group, a N-substituted amino group, a carboxyl group, a carbonyl group, an acid anhydride group, an aldehyde group, a hydroxyl group, an epoxy group, a thiol, a disulfide group, an alkenyl group, a hydrazine group, a hydrazide group, a semicarbazide group, a thiosemicarbazide group, one partner of a binding pair, an amide group, an aryl group, an ester group, an ether group, a glycidyl group, a halo group, a hydride group, an isocyanate group, an urea group, an urethane group, and any combinations thereof.

In some embodiments, the heme-binding molecules and/or compositions disclosed herein can be immobilized on a carrier scaffold for a variety of applications or purposes. For example, the engineered heme-binding molecules and/or compositions can be immobilized on a carrier scaffold for easy handling during usage, e.g., for isolation, observation or microscopic imaging.

The attachment of the heme-binding molecules and/or compositions disclosed herein to a surface of the carrier scaffold can be performed with multiple approaches, for example, by direct cross-linking the engineered heme-binding molecules and/or compositions to the carrier scaffold surface; cross-linking the engineered heme-binding molecule to the carrier scaffold surface via a nucleic acid matrix (e.g., DNA matrix or DNA/oligonucleotide origami structures) for orientation and concentration to increase detection sensitivity; cross-linking the heme-binding molecules and/or compositions to the carrier scaffold surface via a dendrimer-like structure (e.g., PEG/Chitin-structure) to increase detection sensitivity; attracting heme-binding molecules and/or compositions coated magnetic microbeads to the carrier scaffold surface with a focused magnetic field gradient applied to the carrier scaffold surface, attaching an engineered heme-binding molecules and/or compositions to a carrier scaffold via biotin-avidin or biotin-avidin-like interaction, or any other art-recognized methods.

Without limitations, any conjugation chemistry known in the art for conjugating two molecules or different parts of a composition together can be used for conjugating at least one engineered heme-binding molecules and/or compositions to a carrier scaffold. Exemplary coupling molecules and/or functional groups for conjugating at least one engineered heme-binding molecules and/or compositions to a substrate include, but are not limited to, a polyethylene glycol (PEG, NH2-PEG$_X$-COOH which can have a PEG spacer arm of various lengths X, where 1<X<100, e.g., PEG-2K, PEG-5K, PEG-10K, PEG-12K, PEG-15K, PEG-20K, PEG-40K, and the like), maleimide conjugation agent, PASylation, HESylation, Bis(sulfosuccinimidyl) suberate conjugation agent, DNA conjugation agent, peptide conjugation agent, silane conjugation agent, polysaccharide conjugation agent, hydrolyzable conjugation agent, and any combinations thereof.

For engineered heme-binding molecules and/or compositions to be immobilized on or conjugated to a carrier scaffold, the heme-binding molecules and/or compositions described herein can further comprise at least one (e.g., one, two, three, four, five, six, seven, eight, nine, ten, eleven, twelve, thirteen, fourteen, fifteen, sixteen, seventeen, eighteen, nineteen, twenty or more) second domain, e.g., adapted for orienting the heme-binding domain away from the carrier scaffold surface. In some embodiments, the carrier scaffold surface can be functionalized with a coupling molecule to facilitate the conjugation of engineered heme-binding molecules and/or compositions to the solid surface.

Accordingly, in some embodiments, the second domain can be selected or configured to provide one or more functional groups for conjugating the heme-binding domain with a carrier scaffold or a deteactable label. A domain adapted for conjugating the heme-binding molecule to a carrier scaffold is also referred to as a "conjugation domain" herein. As used herein, the term "conjugation domain" refers to any molecule or portion thereof that facilitates the conjugation of the engineered molecules described herein to a carrier scaffold.

In some embodiments, length of the conjugation domain can vary from 1 amino acid residue to about 10 amino acid residues, or about 2 amino acid residues to about 5 amino acid residues. Determination of an appropriate amino acid sequence of the oconjugatio domain for binding with different carrier scaffolds is well within one of skill in the art. For example, according to one or more embodiments, the conjugation domain can comprise an amino acid sequence of AKT (SEQ ID NO: 35), which provides a single biotinylation site for subsequent binding to streptavidin. Preferably the AKT is at the terminus or near the terminus (e.g., within less than 10 amino acids from the terminus) of the heme-binding molecule and/or composition. In some embodiments, the conjugation domain comprises a functional group for conjugating or linking the heme-binding molecule and/or composition to the carrier scaffold. Some exemplary functional groups for conjugation include, but are not limited to, an amino group, a N-substituted amino group, a carboxyl group, a carbonyl group, an acid anhydride group, an aldehyde group, a hydroxyl group, an epoxy group, a thiol, a disulfide group, an alkenyl group, a hydrazine group, a hydrazide group, a semicarbazide group, a thiosemicarbazide group, one partner of a binding pair, an amide group, an aryl group, an ester group, an ether group, a glycidyl group, a halo group, a hydride group, an isocyanate group, an urea group, an urethane group, and any combinations thereof.

Activation agents can be used to activate the components to be conjugated together. Without limitations, any process and/or reagent known in the art for conjugation activation can be used. Exemplary activation methods or reagents include, but are not limited to, 1-Ethyl-3-[3-dimethylaminopropyl]carbodiimide hydrochloride (EDC or EDAC), hydroxybenzotriazole (HOBT), N-Hydroxysuccinimide (NHS), 2-(1H-7-Azabenzotriazol-1-yl)-1,1,3,3-tetramethyl uronium hexafluorophosphate methanaminium (HATU), silanization, surface activation through plasma treatment, and the like.

In some embodiments, the conjugation domain can comprise at least one amino group that can be non-convalently or covalently coupled with functional groups on the carrier scaffold. For example, the primary amines of the amino acid residues (e.g., lysine or cysteine residues) can be used to conjugate the heme-binding molecule and/or composition with the carrier scaffold. In some embodiments, the amino group at the N-terminus of the heme-binding molecules and/or compositions can be used for conjugating the heme-binding molecules and/or compositions with the carrier scaffold.

Without limitations, the engineered heme-binding molecules and/or compositions can be conjugated to the carrier-scaffold through covalent or non-covalent interactions or any combination of covalent and non-covalent interactions.

Further, conjugation can be accomplished any of method known to those of skill in the art. For example, covalent immobilization can be accomplished through, for example, silane coupling. See, e.g., Weetall, 15 *Adv. Mol. Cell Bio.* 161 (2008); Weetall, 44 *Meths. Enzymol.* 134 (1976). The covalent interaction between the engineered heme-binding molecules and/or compositions and/or coupling molecule and the surface can also be mediated by other art-recognized chemical reactions, such as NHS reaction or a conjugation agent. The non-covalent interaction between the engineered heme-binding molecules and/or compositions and/or coupling molecule and the surface can be formed based on ionic interactions, van der Waals interactions, dipole-dipole interactions, hydrogen bonds, electrostatic interactions, and/or shape recognition interactions.

Without limitations, conjugation can include either a stable or a labile (e.g. cleavable) bond or conjugation agent. Exemplary conjugations include, but are not limited to, covalent bond, amide bond, additions to carbon-carbon multiple bonds, azide alkyne Huisgen cycloaddition, Diels-Alder reaction, disulfide linkage, ester bond, Michael additions, silane bond, urethane, nucleophilic ring opening reactions: epoxides, non-aldol carbonyl chemistry, cycloaddition reactions: 1,3-dipolar cycloaddition, temperature sensitive, radiation (IR, near-IR, UV) sensitive bond or conjugation agent, pH-sensitive bond or conjugation agent, non-covalent bonds (e.g., ionic charge complex formation, hydrogen bonding, pi-pi interactions, hist guest interactions, such as cyclodextrin/adamantly host guest interaction) and the like.

In some embodiments, the heme-binding molecules and/or compositions can be conjugated to the carrier-scaffold with a linker. In some embodiments, the heme-binding molecules and/or compositions can be conjugated to the carrier-scaffold with a linking group selected from the group consisting of a direct bond, an atom such as oxygen or sulfur, $C(O)$, $C(O)O$, $OC(O)O$, $C(O)NH$, $NHC(O)O$, $NH$, $SS$, $SO$, $SO_2$, $SO_3$, and $SO_2NH$.

In some embodiments, the engineered heme-binding molecules and/or compositions can be conjugated to the carrier scaffold by a coupling molecule pair. The terms "coupling molecule pair" and "coupling pair" as used interchangeably herein refer to the first and second molecules that specifically bind to each other. One member of the binding pair is conjugated with the carrier scaffold while the second member is conjugated with the heme-binding molecules and/or compositions. As used herein, the phrase "first and second molecules that specifically bind to each other" refers to binding of the first member of the coupling pair to the second member of the coupling pair with greater affinity and specificity than to other molecules. Exemplary coupling molecule pairs include, without limitations, any haptenic or antigenic compound in combination with a corresponding antibody or binding portion or fragment thereof (e.g., digoxigenin and anti-digoxigenin; mouse immunoglobulin and goat antimouse immunoglobulin) and nonimmunological binding pairs (e.g., biotin-avidin, biotin-streptavidin), hormone (e.g., thyroxine and cortisol-hormone binding protein), receptor-receptor agonist, receptor-receptor antagonist (e.g., acetylcholine receptor-acetylcholine or an analog thereof), IgG-protein A, lectin-carbohydrate, enzyme-enzyme cofactor, enzyme-enzyme inhibitor, and complementary oligonucleotide pairs capable of forming nucleic acid duplexes). The coupling molecule pair can also include a first molecule that is negatively charged and a second molecule that is positively charged.

One example of using coupling pair conjugation is the biotin-avidin or biotin-streptavidin conjugation. In this approach, one of the members of molecules to be conjugated together (e.g., the engineered heme-binding molecule and/or composition or the carrier scaffold) is biotinylated and the other is conjugated with avidin or streptavidin. Many commercial kits are available for biotinylating molecules, such as proteins. For example, an aminooxy-biotin (AOB) can be used to covalently attach biotin to a molecule with an aldehyde or ketone group. In some embodiments, AOB is attached to the engineered heme-binding molecule and/or composition. Further, as described elsewhere herein, an AKT sequence on the N-terminal of the engineered heme-binding molecules and/or compositions can allow the engineered heme-binding molecules and/or compositions to be biotinylated at a single site and further conjugated to the streptavidin-coated solid surface. Moreover, the heme-binding molecule and/or composition can be coupled to a biotin acceptor peptide, for example, the AviTag or Acceptor Peptide (referred to as AP; Chen et al., 2 *Nat. Methods* 99 (2005)). The Acceptor Peptide sequence allows site-specific biotinylation by the *E. coli* enzyme biotin ligase (BirA; Id.). Thus, in some embodiments, the conjugation domain comprises an amino acid sequence of a biotin acceptor peptide.

Another non-limiting example of using conjugation with a coupling molecule pair is the biotin-sandwich method. See, e.g., Davis et al., 103 *PNAS* 8155 (2006). In this approach, the two molecules to be conjugated together are biotinylated and then conjugated together using tetravalent streptavidin. Another example for conjugation would be to use PLP-mediated bioconjugation. See, e.g., Witus et al., 132 *JACS* 16812 (2010). Still another example of using coupling pair conjugation is double-stranded nucleic acid conjugation.

In this approach, one of the members of molecules to be conjugated together is conjugated with a first strand of the double-stranded nucleic acid and the other is conjugated with the second strand of the double-stranded nucleic acid. Nucleic acids can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges.

The carrier scaffold can also be functionalized to include a functional group for conjugating with the heme-binding molecules and/or compositions. In some embodiments, the carrier scaffold can be functionalized to include a coupling molecule, or a functional fragment thereof, that is capable of selectively binding with an engineered heme-binding molecules and/or compositions described herein. As used herein, the term "coupling molecule" refers to any molecule or any functional group that is capable of selectively binding with an engineered microbe surface-binding domain described herein. Representative examples of coupling molecules include, but are not limited to, antibodies, antigens, lectins, proteins, peptides, nucleic acids (DNA, RNA, PNA and nucleic acids that are mixtures thereof or that include nucleotide derivatives or analogs); receptor molecules, such as the insulin receptor; ligands for receptors (e.g., insulin for the insulin receptor); and biological, chemical or other molecules that have affinity for another molecule.

In some embodiments, the coupling molecule is an aptamer. As used herein, the term "aptamer" means a single-stranded, partially single-stranded, partially double-stranded or double-stranded nucleotide sequence capable of specifically recognizing a selected non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. Methods for selecting aptamers for binding to a molecule are widely known in the art and easily accessible to one of ordinary skill in the art. The aptamers can be of any length, e.g., from about 1 nucleotide to about 100 nucleotides, from about 5 nucleotides to about 50 nucleotides, or from about 10 nucleotides to about 25 nucleotides.

In some embodiments, the heme-binding composition and/or molecule can further comprise a therapeutic agent. For example, the heme-binding composition and/or molecule can comprise an anti-microbial agent. Therapeutic agents are described herein below. Any method available to the skilled artisan for conjugating a therapeutic agent to a peptide can be used for conjugating the therapeutic agent to the heme-binding composition and/or molecule. For example, functional groups or methods used for conjugating the molecule to a carrier scaffold can also be used for conjugating the molecule to a therapeutic agent. This can be beneficial for delivering or concentrating a therapeutic agent (e.g., an anti-microbial agent) at a nidus of infection.

The multiple domains of a heme-binding molecule and/or composition can be arranged in any desired orientation in the engineered heme-binding molecule and/or composition. For example, N-terminus of the heme-binding domain can be linked to the C-terminus of a second domain or C-terminus of the heme-binding domain can be linked to the N-terminus of a second domain. In some embodiments, that linking between the first and second domain is via the linker.

Further, as disclosed herein, an engineered heme-binding molecules and/or compositions can comprise at least one heme-binding domain, including at least two, at least three, at least four, at least five, at least six, at least seven, at least eight, at least nine, at least ten or more heme-binding domains. When more than two first or second domains are present, such domains can all be the same, all different, or some same and some different.

In some embodiments, the engineered heme-binding molecule and/or composition disclosed herein comprises two or more heme-binding domains and one second domain. In such molecules, one heme-binding domain can be linked to the second domain and the other heme-binding domains can be linked to the heme-binding domain linked to the second domain. Alternatively, two heme-binding domains can be linked to the second domain and other heme-binding domains can be linked to one or both of the two heme-binding domains linked to the second domain.

In some embodiments, the engineered heme-binding molecules and/or compositions disclosed herein comprise two or more second domains and one heme-binding domain. In such molecules, one second domain can be linked to the heme-binding domain and the other second domains can be linked to the second domain linked to the heme-binding domain. Alternatively, two second domains can be linked to the heme-binding domain and other second domains can be linked to one or both of the two second domains linked to the heme-binding domain.

In some embodiments, the engineered heme-binding molecule and/or composition is in the form of a multimeric complex comprising at least two (e.g., two, three, four, five, six, seven, eight, nine, ten, or more) engineered heme-binding molecules and/or compositions. Accordingly, the multimeric complex can be a di-, tri-, tetra-, penta-, hexa- or higher multimeric complex. Without limitations, the multimeric complex can be formed by interactions between a second domain or linker of a first molecule with a second domain or a linker of the second molecule. Such interactions can comprise covalent linking or non-covalent linking. The heme-binding molecules and/or compositions in the multimeric complex can all be the same, all different, or some same and some different.

In some embodiments, an engineered heme-binding molecule can further comprise a substrate binding domain. Non-limiting examples of substrate binding domains can include an Fc domain or AKT.

In some embodiments, a heme-binding composition and/or molecule as described herein can further comprise a microbe-binding domain, e.g. conjugated to and/or in combination with molecules comprising a hemopexin domain. Non-limiting examples of microbe-binding domains can include MBL and CRP. The term "microbe binding domain" can refer to any molecule or a fragment thereof that can specifically bind to the surface of a microbe or pathogen, e.g., any component present on a surface of a microbe or pathogen, or any matter or component/fragment that is derived, originated or secreted from a microbe or pathogen. Molecules that can be used in the microbe binding domain can include, for example, but are not limited to, peptides, polypeptides, proteins, peptidomimetics, antibodies, antibody fragments (e.g., antigen binding fragments of antibodies), carbohydrate-binding protein, e.g., a lectin, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptidoglycan, lipopolysaccharide, small molecules, and any combinations thereof.

Compositions and/or molecules comprising a microbe-binding domain can be used, e.g., for separating microbes from a test sample in vivo, in situ or in vitro. Generally, the microbe-binding molecules disclosed herein can bind with or capture at least one microbe. The microbe can be an intact or whole microbe or any matter or component that is derived, originated or secreted from a microbe. Any matter or component that is derived, originated or secreted from a microbe is also referred to as "microbial matter" herein. Thus, the microbe-binding molecules disclosed herein can bind/capture an intact or whole microbe or microbial matter derived, originated or secreted from the microbe. Exemplary microbial matter that can bind to the microbe-binding molecule can include, but is not limited to, a cell wall component, an outer membrane, a plasma membrane, a ribosome, a microbial capsule, a pili or flagella, any fragments of the aforementioned microbial components, any nucleic acid (e.g., DNA, including 16S ribosomal DNA, and RNA) derived from a microbe, microbial endotoxin (e.g., lipopolysaccharide), and the like. In addition, microbial matter can encompass non-viable microbial matter that can cause an adverse effect (e.g., toxicity) to a host or an environment. The terms "microbe-binding molecule(s)" and "microbe-targeting molecule(s)" are used interchangeably herein.

In accordance with the various embodiments described herein, molecules can comprise at least one microbe-binding domain comprising at least a portion of a C-reactive protein (CRP) and at least one hemopexin domain. In some embodiments, the two domains can be conjugated together via a linker. In addition to the microbe-binding domain amino acid sequence, the molecule can further comprise one or more amino acids (e.g., one, two, three, four, five, six, seven, eight, nine, ten, or more) amino acids on the N- or C-terminus of the microbe-binding sequence. Generally, the microbe-binding domain can have an amino acid sequence of about 10 to about 300 amino acid residues. In some embodiments, the microbe-binding domain can have an amino acid sequence of about 50 to about 250 amino acid residues. In some embodiments, the microbe-binding domain can have an amino acid sequence of at least about 5, at least about 10, at least about 15, at least about 20, at least about 30, at least about 40, at least about 50, at least about 60, at least about 70, at least about 80, at least about 90, at least about 100 amino acid residues or more. For any known sequences of a microbe-binding domain, one of skill in the art can determine the optimum length of amino acid sequence for retaining microbe-binding activity.

C-reactive protein (CRP) can bind with gram-positive microbe and can be used for capturing/detecting microbes. As used herein, "CRP" can comprise full length CRP or a fragment thereof retaining microbe binding activity. Without limitations, the CRP can be from any source available to one of skill in the art. For example, the CRP can be from a mammalian source. For example, the CRP can be human CRP (NCBI Reference Sequence: NP_000558.2) or mouse CRP (NCBI Reference Sequence: NP_031794.3). In some embodiments, the first domain comprises an amino acid sequence comprising amino acids 19-224 of the human. CRP is described further in the art, e.g., in U.S. Patent Application No. 61/917,705 filed Dec. 18, 2013.

In some embodiments, the microbe-binding domain can comprise a peptidomimetic that mimics a molecule or a fragment thereof that can specifically bind to the surface of a microbe or pathogen, or microbial matter. For example, a microbe-binding domain can comprise a peptidomimetic that mimics a carbohydrate recognition domain or a fragment thereof, e.g., carbohydrate recognition domain of MBL or a fragment thereof.

In some embodiments, the microbe-binding domain can be a carbohydrate recognition domain or a fragment thereof of carbohydrate binding protein. The term "carbohydrate recognition domain" as used herein refers to a region, at least a portion of which, can bind to carbohydrates on a surface of microbes or pathogens. In some embodiments, the second domain can comprise at least about 50% of the full length CRD, including at least about 60%, at least about 70%, at least about 80%, at least about 90% or higher, capable of binding to carbohydrates on a microbe surface. In some embodiments, 100% of the carbohydrate recognition domain can be used to bind to microbes or pathogens. In other embodiments, the carbohydrate recognition domain can comprise additional regions that are not capable of carbohydrate binding, but can have other characteristics or perform other functions, e.g., to provide flexibility to the carbohydrate recognition domain when interacting with microbes or pathogens.

Exemplary carbohydrate-binding proteins include, but are not limited to, lectin, collectin, ficolin, mannose-binding lectin (MBL), maltose-binding protein, arabinose-binding protein, and glucose-binding protein. Additional carbohydrate-binding proteins that can be included in the microbe-binding domain described herein can include, but are not limited to, lectins or agglutinins that are derived from a plant, e.g., Galanthus nivalis agglutinin (GNA) from the Galanthus (snowdrop) plant, and peanut lectin. In some embodiments, pentraxin family members (e.g., C-reactive protein) can also be used as a carbohydrate-binding protein. Pentraxin family members can generally bind capsulated microbes. Without limitation, the carbohydrate-binding proteins can be wild-type, recombinant or a fusion protein. The respective carbohydrate recognition domains for such carbohydrate-binding proteins are known in the art, and can be modified for various embodiments of the engineered microbe-binding molecules described herein.

Any art-recognized recombinant carbohydrate-binding proteins or carbohydrate recognition domains can be used in the engineered molecules. For example, recombinant mannose-binding lectins, e.g., but not limited to, the ones disclosed in the U.S. Pat. Nos. 5,270,199; 6,846,649; U.S. Patent Application No. US 2004/0229212; and PCT Application No. WO 2011/090954, filed Jan. 19, 2011, the contents of all of which are incorporated herein by reference, can be used in constructing the molecules and compositions described herein.

In some embodiments, the CRD is from an MBL, a member of the collectin family of proteins. A native MBL is a multimeric structure (e.g., about 650 kDa) composed of subunits, each of which contains three identical polypeptide chains. Each MBL polypeptide chain (containing 248 amino acid residues in length with a signal sequence) comprises a N-terminal cysteine rich region, a collagen-like region, a neck region, and a carbohydrate recognition domain (CRD). The sequence of each region has been identified and is well known in the art, e.g. human MBL is available in the NCBI BLAST database as accession number NP_000233. The CRD of human MBL comprises amino acids 114 to 248 of NP_000233. In some embodiments, the carbohydrate recognition domain of the engineered MBL molecule can comprise a fragment of the CRD. Exemplary amino acid sequences of such fragments include, but are not limited to, ND (SEQ ID NO: 29), EZN (SEQ ID NO: 30: where Z is any amino acid, e.g., P), NEGEPNNAGS (SEQ ID NO: 31) or a fragment thereof comprising EZN, GSDEDCVLL (SEQ ID NO: 32) or a fragment thereof comprising E, and LLLKNGQWNDVPCST (SEQ ID NO: 33) or a fragment thereof comprising ND. Modifications to such CRD fragments, e.g., by conservative substitution, are also within the scope described herein. In some embodiments, the MBL or a fragment thereof used in the engineered molecules described herein can be a wild-type molecule or a recombinant molecule.

In some circumstances, complement or coagulation activation induced by a carbohydrate-binding protein or a fragment thereof can be undesirable depending on various applications, e.g., in vivo administration for treatment of sepsis. In such embodiments, the additional portion of the carbohydrate-binding protein can exclude at least one of complement and coagulation activation regions. By way of example, when the carbohydrate-binding protein is mannose-binding lectin or a fragment thereof, the mannose-binding lectin or a fragment thereof can exclude at least one of the complement and coagulation activation regions located on the collagen-like region. In such embodiments, the mannose-binding lectin or a fragment thereof can exclude at least about one amino acid residue, including at least about two amino acid residues, at least about three amino acid residues, at least about four amino acid residues, at least about five amino acid residues, at least about six amino acid residues, at least about seven amino acid residues, at least about eight amino acid residues, at least about nine amino acid residues, at least about ten amino acid residues or more, around amino acid residue K55 or L56 of MBL (e.g. NCBI Ref Seq: NP_000233) Exemplary amino acid sequences comprising K55 or L56 of MBL that can be excluded from the engineered molecule or compositions described herein include, but are not limited to, EPGQGLR-GLQGPPGKLGPPGNPGPSGS (SEQ ID NO: 19), GKLG (SEQ ID NO: 20), GPPGKLGPPGN (SEQ ID NO: 21), RGLQGPPGKL (SEQ ID NO: 22), GKLGPPGNPGPSGS (SEQ ID NO: 23), GLRGLQGPPGKLGPPGNPGP (SEQ ID NO: 24), or any fragments thereof.

In some embodiments, the additional portion of the carbohydrate-binding proteins can activate the complement system. In alternative embodiments, the additional portion of the carbohydrate-binding protein cannot activate the complement system. In some embodiments, the additional portion of the carbohydrate-binding protein can be selected, configured, or modified such that it does not activate the complement system.

In some embodiments, the microbe-binding domain can comprise a neck region or a fragment thereof from a lectin. By neck region of a lection is meant the portion of the lection than connects the CRD to rest of the molecule. Without wishing to be bound by theory, the neck region can provide flexibility and proper orientation for binding to a microbe surface. When the microbe-binding molecule disclosed herein comprises a neck region and an additional second domain, the neck region can be located between the first domain and the additional second domain, i.e., the neck region can act as a linker for linking the first domain and the additional second domain. In some embodiments, the second domain can comprise one or more (e.g., one, two, three, four, five, six, seven, eight, nine, ten, or more) additional amino acids on the N- or C-terminus of the neck region. In some embodiments, the neck region comprises the amino acid sequence

```
                                        (SEQ ID NO: 25)
PDGDSSLAASERKALQTEMARIKKWLTFSLGKQ, (SEQ ID NO: 26)
APDGDSSLAASERKALQTEMARIKKWLTFSLGKQ, (SEQ ID NO: 27)
PDGDSSLAASERKALQTEMARIKKWLTFSLG,
or (SEQ ID NO: 28)
APDGDSSLAASERKALQTEMARIKKWLTFSLG.
```

Modifications to the microbe-binding domain, e.g., by conservative substitution, are also within the scope described herein. In some embodiments, the microbe-binding domain or a fragment thereof used in the molecules described herein can be a wild-type molecule or a recombinant molecule.

In some embodiments, a molecule and/or composition as described herein can further comprise a detectable label. As used herein, the term "detectable label" refers to a composition capable of producing a detectable signal indicative of the presence of a target. Detectable labels include any composition detectable by spectroscopic, photochemical, biochemical, immunochemical, electrical, optical or chemical means. Suitable labels include fluorescent molecules, radioisotopes, nucleotide chromophores, enzymes, substrates, chemiluminescent moieties, bioluminescent moieties, and the like. As such, a label is any composition detectable by spectroscopic, photochemical, biochemical, immunochemical, electrical, optical or chemical means needed for the methods and devices described herein.

In some embodiments, the detectable label can be an imaging agent or contrast agent. As used herein, the term "imaging agent" refers to an element or functional group in a molecule that allows for the detection, imaging, and/or monitoring of the presence and/or progression of a condition(s), pathological disorder(s), and/or disease(s). The imaging agent can be an echogenic substance (either liquid or gas), non-metallic isotope, an optical reporter, a boron neutron absorber, a paramagnetic metal ion, a ferromagnetic metal, a gamma-emitting radioisotope, a positron-emitting radioisotope, or an x-ray absorber. As used herein the term "contrast agent" refers to any molecule that changes the optical properties of tissue or organ containing the molecule. Optical properties that can be changed include, but are not limited to, absorbance, reflectance, fluorescence, birefringence, optical scattering and the like. In some embodiments, the detectable labels also encompass any imaging agent (e.g., but not limited to, a bubble, a liposome, a sphere, a contrast agent, or any detectable label described herein) that can facilitate imaging or visualization of a tissue or an organ in a subject, e.g., for diagnosis of an infection.

Suitable optical reporters include, but are not limited to, fluorescent reporters and chemiluminescent groups. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound.

Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); Alexa Fluor350™; Alexa Fluor430™; Alexa Fluor488™; Alexa Fluor 532™; Alexa Fluor546™; Alexa Fluor568™; Alexa Fluor594™; Alexa Fluor 633™; Alexa Fluor647™; Alexa Fluor660™; Alexa Fluor680™; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); BG-647; Bimane; Bisbenzamide; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CFDA; CFP—Cyan Fluorescent Protein; Chlorophyll; Chromomycin A; Chromomycin A;

CMFDA; Coelenterazine; Coelenterazine cp; Coelenterazine f; Coelenterazine fcp; Coelenterazine h; Coelenterazine hcp; Coelenterazine ip; Coelenterazine O; Coumarin Phalloidin; CPM Methylcoumarin; CTC; Cy2™; Cy3.1 8; Cy3.5™; Cy3™; Cy5.1 8; Cy5.5™; Cy5™; Cy7™; Cyan GFP; cyclic AMP Fluorosensor (FiCRhR); d2; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); DIDS; Dihydrorhodamine 123 (DHR); DiO (DiOC18(3)); DiR; DiR (DiIC18(7)); Dopamine; DsRed; DTAF; DY-630-NHS; DY-635-NHS; EBFP; ECFP; EGFP; ELF 97; Eosin; Erythrosin; Erythrosin ITC; Ethidium homodimer-1 (EthD-1); Euchrysin; Europium (III) chloride; Europium; EYFP; Fast Blue; FDA; Feulgen (Pararosaniline); FITC; FL-645; Flazo Orange; Fluo-3; Fluo-4; Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura-2, high calcium; Fura-2, low calcium; Genacryl Brilliant Red B; Genacryl Brilliant Yellow 10GF; Genacryl Pink 3G; Genacryl Yellow 5GF; GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indodicarbocyanine (DiD); Indotricarbocyanine (DiR); Intrawhite Cf; JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; LOLO-1; LO-PRO-1; Lucifer Yellow; Mag Green; Magdala Red (Phloxin B); Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin EBG; Oregon Green™; Oregon Green 488-X; Oregon Green™ 488; Oregon Green™ 500; Oregon Green™ 514; Pacific Blue; Pararosaniline (Feulgen); PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26; PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B 540; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycoerythrin (PE); red shifted GFP (rsGFP, S65T); S65A; S65C; S65L; S65T; Sapphire GFP; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; Tetracycline; Tetramethylrhodamine; Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamineIsoThioCyanate); True Blue; Tru-Red; Ultralite; Uranine B; Uvitex SFC; wt GFP; WW 781; XL665; X-Rhodamine; XRITC; Xylene Orange; Y66F; Y66H; Y66W; Yellow GFP; YFP; YO-PRO-1; YO-PRO-3; YOYO-1; and YOYO-3. Many suitable forms of these fluorescent compounds are available and can be used.

Other exemplary detectable labels include luminescent and bioluminescent markers (e.g., biotin, luciferase (e.g., bacterial, firefly, click beetle and the like), luciferin, and aequorin), radiolabels (e.g., 3H, 125I, 35S, 14C, or 32P), enzymes (e.g., galactosidases, glucorinidases, phosphatases (e.g., alkaline phosphatase), peroxidases (e.g., horseradish peroxidase), and cholinesterases), and calorimetric labels such as colloidal gold or colored glass or plastic (e.g., polystyrene, polypropylene, and latex) beads. Patents teaching the use of such labels include U.S. Pat. Nos. 3,817,837, 3,850,752, 3,939,350, 3,996,345, 4,277,437, 4,275,149, and 4,366,241, each of which is incorporated herein by reference.

Suitable echogenic gases include, but are not limited to, a sulfur hexafluoride or perfluorocarbon gas, such as perfluoromethane, perfluoroethane, perfluoropropane, perfluorobutane, perfluorocyclobutane, perfluropentane, or perfluorohexane. Suitable non-metallic isotopes include, but are not limited to, $^{11}$C, $^{14}$C, $^{13}$N, $^{18}$F, $^{123}$I, $^{124}$I, and $^{125}$I. Suitable radioisotopes include, but are not limited to, $^{99}$mTc, $^{95}$Tc, $^{111}$In, $^{62}$Cu, Ga, $^{68}$Ga, and $^{153}$Gd. Suitable paramagnetic metal ions include, but are not limited to, Gd(III), Dy(III), Fe(III), and Mn(II). Suitable X-ray absorbers include, but are not limited to, Re, Sm, Ho, Lu, Pm, Y, Bi, Pd, Gd, La, Au, Au, Yb, Dy, Cu, Rh, Ag, and Ir.

In some embodiments, the radionuclide is bound to a chelating agent or chelating agent-linker attached to the heme-binding molecule and/or composition. Suitable radionuclides for direct conjugation include, without limitation, $^{18}$F, $^{124}$I, $^{125}$I, $^{131}$I, and mixtures thereof. Suitable radionuclides for use with a chelating agent include, without limitation, $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117}$mSn, $^{149}$Pm, $^{153}$Sm, $^{166}$Ho, $^{177}$Lu, $^{186}$Re, $^{188}$Re, $^{211}$At, $^{212}$Bi, and mixtures thereof. Suitable chelating agents include, but are not limited to, DOTA, BAD, TETA, DTPA, EDTA, NTA, HDTA, their phosphonate analogs, and mixtures thereof. One of skill in the art will be familiar with methods for attaching radionuclides, chelating agents, and chelating agent-linkers to molecules such as the heme-binding molecule and/or composition and carrier scaffolds disclosed herein.

Means of detecting such labels are well known to those of skill in the art. Thus, for example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label. Exemplary methods for in vivo detection or imaging of detectable labels include, but are not limited to, radiography, magnetic resonance imaging (MRI), Positron emission tomography (PET), Single-photon emission computed tomography (SPECT, or less commonly, SPET), Scintigraphy, ultrasound, CAT scan, photoacoustic imaging, thermography, linear tomography, poly tomography, zonography, orthopantomography (OPT or OPG), and computed Tomography (CT) or Computed Axial Tomography (CAT scan).

In some embodiments, the detectable label can include an enzyme. Exemplary enzymes for use as detectable labels include, but are not limited to, horseradish peroxidase (HRP), alkaline phosphastase (AP), or any combinations thereof.

In some embodiments, the detectable can include an enzyme substrate (e.g., an microbial enzyme substrate) conjugated to a detectable agent. For example, the detectable agent can be any moiety that, when cleaved from an enzyme substrate by the enzyme, forms a detectable moiety but that is not detectable in its conjugated state. The enzyme substrate, e.g. a microbial enzyme substrate can be a substrate specific for one or more types of microbes to be detected, and it can be selected depending upon what enzymes the microbe possesses or secretes. See, e.g., International Patent Application: WO 2011/103144 for the use of such detectable label in detection of microbes, the content of which is incorporated herein by reference.

In some embodiments, the detectable label is a fluorophore or a quantum dot. Without wishing to be bound by a theory, using a fluorescent reagent can reduce signal-to-noise in the imaging/readout, thus maintaining sensitivity. In some embodiments, the detectable label is a gold particle.

In some embodiments, the detectable label can be configured to include a "smart label", which is undetectable when conjugated to the heme-binding molecules and/or compositions, but produces a color change when released from the engineered molecules in the presence of an enzyme, e.g. a microbial enzyme. Thus, when a microbe binds to the engineered molecules, the microbe releases enzymes that release the detectable label from the engineered molecules. An observation of a color change indicates presence of the microbe in the sample. In some embodiments, the detectable label can be a chromogenic or fluorogenic microbe enzyme substrate so that when a microbe binds to the engineered microbe-targeting molecule, the enzyme that the microbe releases can interact with the detectable label to induce a color change. Examples of such microbe enzyme substrate can include, but are not limited to, indoxyl butyrate, indoxyl glucoside, esculin, magneta glucoside, red-β-glucuronide, 2-methoxy-4-(2-nitrovinyl) phenyl β-D-glu-copyranoside, 2-methoxy-4-(2-nitrovinyl) phenyl β-D-cetamindo-2-deoxyglucopyranoside, and any other art-recognized microbe enzyme substrates. Such embodiments can act as an indicator for the presence of a microbe or pathogen or enzyme.

In one aspect, described herein is a method of reducing the level of free heme in the blood of a subject, the method comprising contacting the blood of the subject with a heme-binding composition as described herein. In some embodiments, the method can comprise administering the composition to the subject. In some embodiments, the method can comprise removing a portion of the subject's blood prior to the contacting step and performing the contacting step extracorporeally and then returning the portion of the subject's blood to the subject.

In some embodiments, the heme-binding compositions described herein, e.g. the compositions comprising the hemopexin polypeptides described herein can bind to myoglobin.

In one aspect, described herein is a method of reducing the level of free myoglobin in the blood of a subject, the method comprising contacting the blood of the subject with a heme-binding composition as described herein. In some embodiments, the method can comprise administering the composition to the subject. In some embodiments, the method can comprise removing a portion of the subject's blood prior to the contacting step and performing the contacting step extracorporeally and then returning the portion of the subject's blood to the subject.

In some embodiments, described herein is a method of treating, e.g. crush injury and/or rhabdomyolysis in a subject by administering a heme-binding molecule and/or composition as described herein to the subject. Rhabdomyolysis can arise from a number of causes, e.g. crush injury, infections, toxins, etc. and cause kidney damage. In some embodiments, administration can comprise contacting the blood of the subject with the heme-binding molecule and/or composition. In some embodiments, the method can comprise administering the molecule and/or composition to the subject. In some embodiments, the method can comprise removing a portion of the subject's blood prior to the contacting step and performing the contacting step extracorporeally and then returning the portion of the subject's blood to the subject.

In some embodiments, the extracorporeal device is a device as described in, e.g. International Patent Publications WO2012/135834 and WO2011/091037; each of which is incorporated by reference herein in its entirety. Further extracorporeal devices for blood filtration and methods of constructing them are well known in the art, see, e.g. International Patent Publications PCT/US04/012911; PCT/US05/065126; PCT/USO4/040923; PCT/SE87/006471; PCT/IB11/056000; PCT/US90/006924; PCT/US06/0016747; PCT/JP10/072557; U.S. Patent Publications 2011/0272343; 2012/0220915 and U.S. Pat. Nos. 3,954,623; 7,059,480; 7,217,365; 7,014,648; 4,517,090; 7,488,302; 7,332,096; each of which is incorporated by reference herein in its entirety. By way of non-limiting example, the device can comprise a blood removal means, e.g. a needle and attached tubing, a filtration unit, and a blood return means, e.g. a second tubing and needle. The filtration unit can comprise a substrate with a large surface area, e.g. a filter, column, membrane, porous surface, channels, and the like. Blood filtration devices can optionally further comprise pumps, syringes, blood storage compartments, reservoirs, tubing, sterilization means, and the like.

In some embodiments, the extracorporeal device can comprise a heme-binding molecule and/or composition as described herein conjugated to a hollow fiber DLT-like device, e.g. the HEMOPURIFIER™ device (Aethlon Medical; San Diego, Calif.). Further information can be found in the art at, e.g., U.S. Pat. Nos. 6,254,567; 8,105,487; 6,117,100; U.S. Patent Publication 2012/0164628; International Patent Publication WO2012135834; WO2006041125; WO2010065765; and European Patent No. 2694970, 2344233; 1624785.

In one aspect, described herein is a composition comprising a heme-binding molecule or composition as described herein, and further comprising a solid substrate or support to which the heme-binding molecule or composition is conjugated. In some embodiments, the solid substrate or support can be a hollow fiber, e.g. the hollow fiber of a DLT device, as described above herein.

In some embodiments, the heme-binding composition is bound to a solid substrate of an extracorporeal device, e.g. a filter, affinity column, cavity or tube. Non-limiting examples of solid substrate include a hollow-fiber reactor or any other blood filtration membrane or flow device (e.g., a simple dialysis tube) or other resins, fibers, or sheets to which the heme-binding composition can be bound. In some embodiments, binding can be non-covalent, e.g., by hydrogen, electrostatic, or van der waals interactions, however, binding may also be covalent. By "conjugated" is meant the covalent linkage of at least two molecules. In some embodiments, the heme-binding composition can be conjugated to a protein on the solid substrate.

In some embodiments, the heme-binding molecule and/or composition can be bound to, e.g. a bead or particle. The beards and/or particles can be contacted with the subject's blood. Heme present in the blood will be bound by the heme-binding molecule and/or composition and the complex of heme and heme-binding molecule and/or composition can then be removed from the blood by, e.g. centrifugation to pellet the beads or applying magnetic field to separate magnetic beads from the blood. As used herein, the term "bead" refers to a microparticle of any design or construction, but preferably a microparticle that is about the size of a cell or smaller. While cell sizes vary according to cell type, the bead (microparticles) can be of any such size or smaller, e.g. nanoscale in size. In some embodiments, the beads or particles can range in size from 1 nm to 1 mm. In some embodiments, the beads can be about 250 nm to about 250 µm in size.

The bead can be formed of any material to which a heme-binding molecule and/or composition can be bound. Suitable materials include, without limitation, a synthetic polymer, biopolymer, latex, or silica, and the material may have paramagnetic properties. The use of such beads and/or particles is known in the art and described, e.g. magnetic bead and nano-particles are well known and methods for their preparation have been described in the are art, for example in U.S. Pat. Nos. 6,878,445; 5,543,158; 5,578,325; 6,676,729; 6,045,925 and 7,462,446, and U.S. Pat. Pub. Nos.: 2005/0025971; 2005/0200438; 2005/0201941; 2005/0271745; 2006/0228551; 2006/0233712; 2007/01666232 and 2007/0264199, contents of all of which are herein incorporated by reference in their entirety. Magnetic microbeads are easily and widely available commercially, with or without functional groups capable of binding to affinity molecules. Suitable superparamagnetic microbeads are commercially available such as from Dynal Inc. of Lake Success, N. Y.; PerSeptive Diagnostics, Inc. of Cambridge, Mass.; Invitrogen Corp. of Carlsbad, Calif.; Cortex Biochem Inc. of San Leandro, Calif.; and Bangs Laboratories of Fishers, Ind.

In some embodiments, provided herein is an article or product for targeting or binding microbes comprising at least one, including at least two, at least three, at least four, at least five, at least ten, at least 25, at least 50, at least 100, at least 250, at least 500, or more engineered heme-binding molecules and/or compositions conjugated to a carrier scaffold or a surface thereof. The "carrier scaffold" is also referred to as a "carrier substrate" herein. In some embodiments, surface of the carrier scaffold can be coated with the heme-binding molecules and/or compositions disclosed herein. As used herein, the term "article" refers to any distinct physical microscale or macroscale object. An article comprising a heme-binding molecule and/or composition conjugated to a carrier scaffold is also referred to as a "heme-binding article" herein.

Without limitations, the carrier scaffold can be selected from a wide variety of materials and in a variety of formats. For example, the carrier scaffold can be utilized in the form of beads or particles (including nanoparticles, microparticles, polymer microbeads, magnetic microbeads, and the like), filters, fibers, screens, mesh, tubes, hollow fibers, scaffolds, plates, channels, gold particles, magnetic materials, planar shapes (such as a rectangular strip or a circular disk, or a curved surface such as a stick), other substrates commonly utilized in assay formats, and any combinations thereof.

Examples of carrier scaffolds include, but are not limited to, nucleic acid scaffolds, protein scaffolds, lipid scaffolds, dendrimers, microparticles or microbeads, nanotubes, microtiter plates, medical apparatuses (e.g., needles or catheters) or implants, dipsticks or test strips, microchips, filtration devices or membranes, membranes, diagnostic strips, hollow-fiber reactors, microfluidic devices, living cells and biological tissues or organs, extracorporeal devices, mixing elements (e.g., spiral mixers), and the like. In some embodiments, the carrier scaffold can be in the form of a continuous roll on which the test area(s) and optionally reference area(s) are present in the form of continuous lines or a series of spots.

The carrier scaffold can be made of any material, including, but not limited to, metal, metal alloy, polymer, plastic, paper, glass, fabric, packaging material, biological material such as cells, tissues, hydrogels, proteins, peptides, nucleic acids, and any combinations thereof.

In some embodiments, the heme-binding articles disclosed herein can be used to capture, detect, or remove heme and/or myoglobin from any source or in any fluid, e.g., a biological fluid (e.g., blood sample). In some embodiments where the fluid is blood, after removal of the heme and/or myoglobin from the blood collected from a subject with the heme-binding magnetic microbeads, the blood can be circulated back to the same subject as a therapeutic intervention. Alternatively, the carrier scaffold can comprise a hollow-fiber reactor or any other blood filtration membrane or flow device (e.g., a simple dialysis tube, spiral mixer or static mixer) or other resins, fibers, or sheets to selective bind and sequester the heme and/or myoglobin.

The particular format or material of the carrier scaffold depends on the particular use or application, for example, the separation/detection methods employed in an assay application. In some embodiments, the format or material of the carrier scaffold can be chosen or modified to maximize signal-to-noise ratios, e.g., to minimize background binding or for ease of separation of reagents and cost. For example, carrier scaffold can be treated or modified with surface chemistry to minimize chemical agglutination and non-specific binding. In some embodiments, at least a portion of the carrier scaffold surface that is in contact with a test sample can be treated to become less adhesive to any molecules (including microbes, if any) present in a test sample. By way of example only, the carrier scaffold surface in contact with a test sample can be salinized or coated with a polymer such that the surface is inert to the molecules present in the test sample, including but not limited to, cells or fragments thereof (including blood cells and blood components), proteins, nucleic acids, peptides, small molecules, therapeutic agents, microbes, microorganisms and any combinations thereof. In other embodiments, a carrier scaffold surface can be treated with an omniphobic layer. See, e.g., Wong T S et al., "Bioinspired self-repairing slippery surfaces with pressure-stable omniphobicity." (2011) *Nature* 477 (7365): 443-447, and International Application No.: PCT/US12/21928, the content of which is incorporated herein by reference, for methods to produce a slippery carrier scaffold surface. Accordingly, non-specific binding of molecules from the test sample to a substrate surface can be reduced, thus increasing the sensitivity and specificity of the heme-binding agent.

In some embodiments, the carrier scaffold can be fabricated from or coated with a biocompatible material. As used herein, the term "biocompatible material" refers to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood. Suitable biocompatible materials include, for example, derivatives and copolymers of polyimides, poly(ethylene glycol), polyvinyl alcohol, polyethyleneimine, and polyvinylamine, polyacrylates, polyamides, polyesters, polycarbonates, and polystyrenes. In some embodiments, biocompatible materials can include metals, such as titanium and stainless steel, or any biocompatible metal used in medical implants. In some embodiments, biocompatible materials can include paper substrate, e.g., as a carrier scaffold for a diagnostic strip. In some embodiments, biocompatible materials can include peptides or nucleic acid molecules, e.g., a nucleic acid scaffold such as a 2-D DNA sheet or 3-D DNA scaffold.

Additional material that can be used to fabricate or coat a carrier scaffold include, without limitations, polydimethylsiloxane, polyimide, polyethylene terephthalate, polymethylmethacrylate, polyurethane, polyvinylchloride, polystyrene polysulfone, polycarbonate, polymethylpentene, polypropylene, polyvinylidine fluoride, polysilicon, polytetrafluoroethylene, polysulfone, acrylonitrile butadiene styrene, polyacrylonitrile, polybutadiene, poly(butylene terephthalate), poly(ether sulfone), poly(ether ether ketones), poly(ethylene glycol), styrene-acrylonitrile resin, poly(trimethylene terephthalate), polyvinyl butyral, polyvinylidenedifluoride, poly(vinyl pyrrolidone), and any combination thereof.

In some embodiments, the carrier scaffold can be fabricated from or coated with a biodegradable material. As used herein, the term "biodegradable" refers to the ability of a composition to erode or degrade in vivo to form smaller chemical fragments. Degradation can occur, for example, by enzymatic, chemical or physical processes. Non-limiting examples of biodegradable polymers that can be used in aspects provided herein include poly(lactide)s, poly(glycolide)s, poly(lactic acid)s, poly(glycolic acid)s, poly (lactide-co-glycolide), polyanhydrides, polyorthoesters, polycaprolactone, polyesteramides, polycarbonate, polycyanoacrylate, polyurethanes, polyacrylate, blends and copolymers thereof.

Other additional biodegradable polymers include biodegradable polyetherester copolymers. Generally speaking, the polyetherester copolymers are amphiphilic block copolymers that include hydrophilic (for example, a polyalkylene glycol, such as polyethylene glycol) and hydrophobic blocks (for example, polyethylene terephthalate). An exemplary block copolymer is, but is not limited to, poly(ethylene glycol)-based and poly(butylene terephthalate)-based blocks (PEG/PBT polymer). PEG/PBT polymers are commercially available from OctoPlus Inc, under the trade designation PolyActive™. Non-limiting examples of biodegradable copolymers or multiblock copolymers include the ones described in U.S. Pat. Nos. 5,980,948 and 5,252,701, the contents of which are incorporated herein by reference.

Other biodegradable polymer materials include biodegradable terephthalate copolymers that include a phosphorus-containing linkage. Polymers having phosphoester linkages, called poly(phosphates), poly(phosphonates) and poly(phosphites), are known in the art. See, for example, Penczek et al., *Handbook of Polymer Synthesis*, Chapter 17: "Phosphorus-Containing Polymers," 1077-1 132 (Hans R. Kricheldorf ed., 1992), as well as U.S. Pat. Nos. 6,153,212; 6,485,737; 6,322,797; 6,600,010; 6,419,709; 6,419,709; 6,485,737; 6,153,212; 6,322,797 and 6,600,010, the contents of which are incorporated herein by reference.

Biodegradable polyhydric alcohol esters can also be used as a material of a carrier scaffold (e.g., a microparticle) (See U.S. Pat. No. 6,592,895, which is incorporated herein by reference). In some embodiments, the biodegradable polymer can be a three-dimensional crosslinked polymer network containing hydrophobic and hydrophilic components which forms a hydrogel with a crosslinked polymer structure, such as the one described in U.S. Pat. No. 6,583,219. In yet further embodiments, the biodegradable polymer can comprise a polymer based upon α-amino acids (such as elastomeric copolyester amides or copolyester urethanes, as described in U.S. Pat. No. 6,503,538, which is incorporated herein by reference).

In some embodiments, the carrier scaffold can comprise a paper, nitrocellulose, glass, plastic, polymer, membrane material, nylon, and any combinations thereof. This is useful for using the article as a test strip of a dipstick.

As used herein, by the "coating" or "coated" is generally meant a layer of molecules or material formed on an outermost or exposed layer of a surface. With respect to a coating of engineered heme-binding molecules and/or compositions on a carrier scaffold, the term "coating" or "coated" refers to a layer of engineered heme-binding molecules and/or compositions formed on an outermost or exposed layer of a carrier scaffold surface. In some embodiments, the carrier scaffold surface can encompass an outer surface or an inner surface, e.g., with respect to a hollow structure.

The amount of the engineered heme-binding molecules and/or compositions conjugated to or coating on a carrier scaffold can vary with a number of factors such as a surface area, conjugation/coating density, types of engineered heme-binding molecules and/or compositions, and/or binding performance. A skilled artisan can determine the optimum density of engineered heme-binding molecules and/or compositions on a carrier scaffold using any methods known in the art. By way of example only, for magnetic microparticles as a carrier scaffold, the amount of the engineered heme-binding molecules and/or compositions used for conjugating to or coating magnetic microparticles can vary from about 1 wt % to about 30 wt %, or from about 5 wt % to about 20 wt %. In some embodiments, the amount of the engineered heme-binding molecules and/or compositions used for conjugating to or coating magnetic microparticles can be higher or lower, depending on a specific need. However, it should be noted that if the amount of the engineered heme-binding molecules and/or compositions used for conjugating to or coating the magnetic microparticles is too low, the magnetic microparticles can show a lower binding performance with heme and/or myoglobin. On the contrary, if the amount of the engineered heme-binding molecules and/or compositions used for conjugating to or coating the magnetic microparticles is too high, the dense layer of the engineered heme-binding molecules and/or compositions can exert an adverse influence on the magnetic properties of the magnetic microbeads, which in turn can degrade the efficiency of separating the magnetic microbeads from a fluid utilizing the magnetic field gradient. Similar concerns apply to other substrate types.

In some embodiments, the carrier scaffold can further comprise at least one area adapted for use as a reference area. By way of example only, the reference area can be adapted for use as a positive control, negative control, a reference, or any combination thereof. In some embodiments, the carrier scaffold can further comprise at least two areas, wherein one area is adapted for a positive control and the second area is adapted for a negative control.

In some embodiments, the carrier scaffold can further comprise at least one reference area or control area for comparison with a readout signal determined from the test area. The reference area generally excludes the engineered heme-binding molecules and/or compositions, e.g., to account for any background signal. In some embodiments, the reference area can include one or more known amounts of the detectable label that the engineered heme-binding molecules and/or compositions in the test area encompass. In such embodiments, the reference area can be used for calibration such that the amount of heme and/or myoglobin in a test sample can be estimated or quantified.

In some embodiments, the carrier scaffold can further comprise a detectable label. The detectable label can be separate from the heme-binding molecules and/or compositions conjugated with the carrier scaffold or linked to the heme-binding molecules and/or compositions conjugated with the carrier scaffold.

Heme-binding microparticles: In some embodiments, the carrier scaffold is a microparticle. Accordingly, some embodiments described herein provide a heme-binding microparticle comprising at least one engineered heme-binding molecules and/or compositions on its surface. The term "microparticle" as used herein refers to a particle having a particle size of about 0.001 µm to about 1000 µm, about 0.005 µm to about 50 µm, about 0.01 µm to about 25 µm, about 0.05 µm to about 10 µm, or about 0.05 µm to about 5 µm. In one embodiment, the microparticle has a particle size of about 0.05 µm to about 1 µm. In one embodiment, the microparticle is about 0.09 µm-about 0.2 µm in size.

In some embodiments, the microparticle can range in size from 1 nm to 1 mm, about 2.5 nm to about 500 µm, or about 5 nm to about 250 µm in size. In some embodiments, microparticle can be about 5 nm to about 100 µm in size. In some embodiments, microparticle can be about 0.01 µm to about 10 µm in size. In some embodiments, the microparticle can be about 0.05 µm to about 5 µm in size. In some embodiments, the microparticle can be about 0.08 µm to about 1 µm in size. In one embodiment, the microparticle can be about 10 nm to about 10 µm in size. In some embodiments, the the microparticle can be about 1 nm to about 1000 nm, from about 10 nm to about 500 nm, from about 25 nm to about 300 nm, from about 40 nm to about 250 nm, or from about 50 nm to about 200 nm. In one embodiment, the microparticle can be about 50 nm to about 200 nm.

It will be understood by one of ordinary skill in the art that microparticles usually exhibit a distribution of particle sizes around the indicated "size." Unless otherwise stated, the term "size" as used herein refers to the mode of a size distribution of microparticles, i.e., the value that occurs most frequently in the size distribution. Methods for measuring the microparticle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

Without limitations, the microparticle can be of any shape. Thus, the microparticle can be, but is not limited to, spherical, rod, elliptical, cylindrical, disc, and the like. In some embodiments, the term "microparticle" as used herein can encompass a microsphere. The term "microsphere" as used herein refers to a microparticle having a substantially spherical form. A substantially spherical microparticle is a microparticle with a difference between the smallest radii and the largest radii generally not greater than about 40% of the smaller radii, and more typically less than about 30%, or less than 20%.

In some embodiments, the microparticles having a substantially spherical shape and defined surface chemistry can be used to minimize chemical agglutination and non-specific binding.

In one embodiment, the term "microparticle" as used herein encompasses a microcapsule. The term "microcapsule" as used herein refers to a microscopic capsule that contains an active ingredient, e.g., a therapeutic agent or an imagining agent. Accordingly, in some embodiments, the microparticles comprising on their surface engineered heme-binding molecules and/or compositions can encapsulate at least one active ingredient therein, e.g., a therapeutic agent.

In general, any biocompatible material well known in the art for fabrication of microparticles can be used in embodiments of the microparticle described herein. Accordingly, a microparticle comprising a lipidic microparticle core is also within the scope described herein. An exemplary lipidic microparticle core is, but is not limited to, a liposome. A liposome is generally defined as a particle comprising one or more lipid bilayers enclosing an interior, e.g., an aqueous interior. In one embodiment, a liposome can be a vesicle formed by a bilayer lipid membrane. Methods for the preparation of liposomes are well described in the art, e.g., Szoka and Papahadjopoulos (1980) *Ann. Rev. Biophys. Bioeng.* 9: 467, Deamer and Uster (1983) Pp. 27-51 In: *Liposomes*, ed. M. J. Ostro, Marcel Dekker, New York.

Heme-binding magnetic microparticles: In some embodiments, the microparticle is a magnetic microparticle. Thus, in some embodiments, provided herein is a "heme-binding magnetic microparticle" wherein a magnetic microparticle comprising on its surface at least one engineered heme-binding molecule and/or composition. Without limitations, such heme-binding magnetic microparticles can be used to separate heme and/or myoglobin from a test sample, e.g., but not limited to, any fluid, including a biological fluid such as blood. In some embodiments, the heme-binding magnetic microparticle can be used to remove heme and/or myoglobin. Using magnetic microparticles as a substrate can be advantageous because the heme-bound magnetic microparticles can be easily separated from a sample fluid using a magnetic field gradient, be examined for the presence of the heme and/or myoglobin. Thus, in some embodiments, the heme-binding magnetic microparticles can be used to capture, detect, or remove heme and/or myoglobin contaminants from any source or in any fluid, e.g., a biological fluid (e.g., blood sample). In some embodiments where the fluid is blood, after removal of the heme and/or my from the blood collected from a subject with the heme-binding magnetic microbeads, the blood can be circulated back to the same subject as a therapeutic intervention. Alternatively, the solid substrate can comprise a hollow-fiber reactor or any other blood filtration membrane or flow device (e.g., a simple dialysis tube, spiral mixer or static mixer) or other resins, fibers, or sheets to selective bind and sequester heme and/or myoglobin.

Magnetic microparticles can be manipulated using magnetic field or magnetic field gradient. Such particles commonly consist of magnetic elements such as iron, nickel and cobalt and their oxide compounds. Magnetic microparticles are well-known and methods for their preparation have been described in the art. See, e.g., U.S. Pat. Nos. 6,878,445; 5,543,158; 5,578,325; 6,676,729; 6,045,925; and 7,462,446; and U.S. Patent Publications No. 2005/0025971; No. 2005/0200438; No. 2005/0201941; No. 2005/0271745; No. 2006/0228551; No. 2006/0233712; No. 2007/01666232; and No. 2007/0264199, the contents of which are incorporated herein by reference.

Magnetic microparticles are also widely and commercially available, with or without functional groups capable of conjugation with the heme-binding molecules and/or compositions disclosed herein. Magnetic microparticles functionalized with various functional groups, e.g., amino groups, carboxylic acid groups, epoxy groups, tosyl groups, or silica-like groups, are also widely and commercially available. Suitable magnetic microparticles are commercially available such as from AdemTech, Miltenyi, PerSeptive Diagnostics, Inc. (Cambridge, Mass.); Invitrogen Corp. (Carlsbad, Calif.); Cortex Biochem Inc. (San Leandro, Calif.); and Bangs Laboratories (Fishers, Ind.). In particular embodiments, magnetic microparticles that can be used herein can be any DYNABEADS® magnetic microbeads (Invitrogen Inc.), depending on the substrate surface chemistry.

Heme-binding microtiter plates: In some embodiments, the bottom surface of microtiter wells can be coated with the engineered heme-binding molecules and/or compositions described herein, e.g., for detecting and/or determining the amount of heme and/or myoglobin in a sample. After heme and/or myoglobin in the sample binding to the engineered heme-binding molecules and/or compositions bound to the microwell surface, the rest of the sample can be removed. Detectable molecules that can also bind to heme and/or myoglobin (e.g., an engineered heme-binding molecules and/or compositions conjugated to a detectable molecule as described herein) can then be added to the microwells with for detection of heme and/or myoglobin. Various signal detection methods for determining the amount of proteins, e.g., using enzyme-linked immunosorbent assay (ELISA), with different detectable molecules have been well established in the art, and those signal detection methods can also be employed herein to facilitate detection of the signal induced by heme and/or myoglobin binding on the engineered heme-binding molecules and/or compositions.

Heme-binding dipsticks/test strips: In some embodiments, the carrier scaffold having the heme-binding molecules and/or compositions conjugated thereon can be in the form of a dipstick and/or a test strip for capture, detection, or clearance of heme and/or myoglobin. For example, a dipstick and/or a test strip can include at least one test area containing one or more engineered heme-binding molecules and/or compositions described herein. The dipstick and/or a test strip can be in any shape and/or in any format, e.g., a planar shape such as a rectangular strip or a circular disk, or a curved surface such as a stick. Alternatively, a continuous roll can be utilized, rather than discrete test strips, on which the test area(s) and optionally reference area(s) are present in the form of continuous lines or a series of spots. In some embodiments, the heme-binding dipsticks or test strips described herein can be used as point-of-care diagnostic tools for heme and/or myoglobin.

In some embodiments, the carrier scaffold in the form of a dipstick or a test strip can be made of any material, including, without limitations, paper, nitrocellulose, glass, plastic, polymer, membrane material, nylon, and any combinations thereof. In one embodiment, the carrier scaffold in the form of a dipstick or a test strip can include paper. In one embodiment, the carrier scaffold in the form of a dipstick or a test strip can include nylon.

In some embodiments, the dipstick or a test strip can further comprise at least one reference area or control area for comparison with a readout signal determined from the test area. The reference area generally excludes the engineered heme-binding molecules and/or compositions, e.g., to account for any background signal. In some embodiments, the reference area can include one or more known amounts of the detectable label that the engineered heme-binding molecules and/or compositions in the test area encompass. In such embodiments, the reference area can be used for calibration such that the amount of heme and/or myoglobin in a test sample can be estimated or quantified.

In some embodiments, the dipstick/test strip can further comprise a detectable label as described herein. The detectable label can be linked to the heme-binding molecule conjugated with the dipstick/test strip or separate from the heme-binding molecule conjugated with the dipstick/test strip.

In one embodiment, about 1 µg to about 100 µg heme-binding molecules can be coated on or attached to a dipstick or membrane surface. In another embodiment, about 3 µg to about 60 µg heme-binding molecules can be coated on or attached to a dipstick or membrane surface. In some embodiments, about 0.1 mg/mL to about 50 mg/mL, about 0.5 mg/mL to about 40 mg/mL, about 1 mg/mL to about 30 mg/mL, about 5 mg/mL to about 20 mg/mL heme-binding molecules and/or compositions can be coated on or attached to a dipstick or membrane surface.

In one aspect, described herein is a method of producing a heme-binding molecule and/or composition, the method comprising culturing a cell comprising a nucleic acid, e.g. an isolated nucleic acid, encoding a heme-binding molecule and/or composition as described herein under conditions suitable for the production of proteins and purifying the heme-binding molecule and/or composition by affinity purification with a Fc domain binding reagent.

A nucleic acid encoding a heme-binding molecule and/or composition can be a nucleic acid encoding, e.g. SEQ ID NO: 4 or SEQ ID NO: 5. Nucleic acid molecules encoding a heme-binding molecule and/or composition described herein are prepared by a variety of methods known in the art. These methods include, but are not limited to, PCT, ligation, and direct synthesis. A nucleic acid sequence encoding a polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, N Y, 1982 and 1989), and Ausubel, 1987, 1993, and can be used to construct nucleic acid sequences which encode a heme-binding molecule and/or composition polypeptide as described herein.

The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., Proc. Natl. Acad. Sci. USA (1995) 92:1292).

In one aspect, the technology described herein relates to an expression vector comprising a nucleic acid encoding any of the heme-binding molecule and/or composition polypeptides described herein. Such vectors can be used, e.g. to transform a cell in order to produce the encoded polypeptide. As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in mammalian cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. Vectors useful for the delivery of a sequence encoding an isolated peptide as described herein can include one or more regulatory elements (e.g., promoter, enhancer, etc.) sufficient for expression of the isolated peptide in the desired target cell or tissue. The regulatory elements can be chosen to provide either constitutive or regulated/inducible expression. As used herein, the term "viral vector" refers to a nucleic acid vector construct that includes at least one element of viral origin and has the capacity to be packaged into a viral vector particle. The viral vector can contain the nucleic acid encoding an antibody or antigen-binding portion thereof as described herein in place of non-essential viral genes. The vector and/or particle may be utilized for the purpose of transferring any nucleic acids into cells either in vitro or in vivo. Numerous forms of viral vectors are known in the art.

Examples of vectors useful in delivery of nucleic acids encoding isolated peptides as described herein include plasmid vectors, non-viral plasmid vectors (e.g. see U.S. Pat. Nos. 6,413,942, 6,214,804, 5,580,859, 5,589,466, 5,763,270 and 5,693,622, all of which are incorporated herein by reference in their entireties); retroviruses (e.g. see U.S. Pat. No. 5,219,740; Miller and Rosman (1989) BioTechniques 7:980-90; Miller, A. D. (1990) Human Gene Therapy 1:5-14; Scarpa et al. (1991) Virology 180:849-52; Miller et al., Meth. Enzymol. 217:581-599 (1993); Burns et al. (1993) Proc. Natl. Acad. Sci. USA 90:8033-37; Boris-Lawrie and Temin (1993) Curr. Opin. Genet. Develop. 3:102-09. Boesen et al., Biotherapy 6:291-302 (1994); Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993), the contents of each of which are herein incorporated by reference in their entireties); lentiviruses (e.g., see U.S. Pat. Nos. 6,143,520; 5,665,557; and 5,981,276, the contents of which are herein incorporated by reference in their entireties; adenovirus-based expression vectors (e.g., see Haj-Ahmad and Graham (1986) J. Virol. 57:267-74; Bett et al. (1993) J. Virol. 67:5911-21; Mittereder et al. (1994) Human Gene Therapy 5:717-29; Seth et al. (1994) J. Virol. 68:933-40; Barr et al. (1994) Gene Therapy 1:51-58; Berkner, K. L. (1988) BioTechniques 6:616-29; and Rich et al. (1993) Human Gene Therapy 4:461-76; Wu et al. (2001) Anesthes. 94:1119-32; Parks (2000) Clin. Genet. 58:1-11; Tsai et al. (2000) Curr. Opin. Mol. Ther. 2:515-23; and U.S. Pat. Nos. 6,048,551; 6,306,652 and 6,306,652, incorporated herein by reference in their entireties); Adeno-associated viruses (AAV) (e.g. see U.S. Pat. Nos. 5,139,941; 5,622,856; 5,139,941; 6,001,650; and 6,004,797, the contents of each of which are incorporated by reference herein in their entireties); and avipox vectors (e.g. see WO 91/12882; WO 89/03429; and WO 92/03545; which are incorporated by reference herein in their entireties).

Useful methods of transfection can include, but are not limited to electroporation, sonoporation, protoplast fusion, peptoid delivery, or microinjection. See, e.g., Sambrook et al (1989) Molecular Cloning, A Laboratory Manual, Cold Spring Harbor Laboratories, New York, for a discussion of techniques for transforming cells of interest; and Felgner, P. L. (1990) Advanced Drug Delivery Reviews 5:163-87, for a review of delivery systems useful for gene transfer. Exemplary methods of delivering DNA using electroporation are described in U.S. Pat. Nos. 6,132,419; 6,451,002, 6,418,341, 6,233,483, U.S. Patent Publication No. 2002/0146831, and International Publication No. WO/0045823, all of which are incorporated herein by reference in their entireties.

Non-limiting examples of vectors useful for expression in prokaryotic cells can include plasmids. Plasmid vectors can include, but are not limited to, pBR322, pBR325, pACYC177, pACYC184, pUC8, pUC9, pUC18, pUC19, pLG339, pR290, pKC37, pKC101, SV 40, pBluescript II SK +/− or KS+/− (see "Stratagene Cloning Systems" Catalog (1993) from Stratagene, La Jolla, Calif, which is hereby incorporated by reference), pQE, pIH821, pGEX, pET series (see Studier et. al., "Use of T7 RNA Polymerase to Direct Expression of Cloned Genes," *Gene Expression Technology*, vol. 185 (1990), which is hereby incorporated by reference in its entirety). Non-limiting examples of mammalian and insect appropriate vectors can include pcDNA3, pCMV6, pOptiVec, pFUSE, and pFastBac.

In some embodiments, the polypeptide can be constitutively expressed. In some embodiments, nucleic acids encoding the polypeptide can be operatively linked to a constitutive promoter. In some embodiments, the polypeptide can be inducibly expressed. In some embodiments, nucleic acids encoding the polypeptide can be operatively linked to an inducible promoter. As described herein, an "inducible promoter" is one that is characterized by initiating or enhancing transcriptional activity when in the presence of, influenced by, or contacted by an inducer or inducing agent than when not in the presence of, under the influence of, or in contact with the inducer or inducing agent. An "inducer" or "inducing agent" may be endogenous, or a normally exogenous compound or protein that is administered in such a way as to be active in inducing transcriptional activity from the inducible promoter. In some embodiments, the inducer or inducing agent, e.g., a chemical, a compound or a protein, can itself be the result of transcription or expression of a nucleic acid sequence (e.g., an inducer can be a transcriptional repressor protein), which itself may be under the control or an inducible promoter. Non-limiting examples of inducible promoters include but are not limited to, the lac operon promoter, a nitrogen-sensitive promoter, an IPTG-inducible promoter, a salt-inducible promoter, and tetracycline, steroid-responsive promoters, rapamycin responsive promoters and the like. Inducible promoters for use in prokaryotic systems are well known in the art, see, e.g. the beta.-lactamase and lactose promoter systems (Chang et al., Nature, 275: 615 (1978, which is incorporated herein by reference); Goeddel et al., Nature, 281: 544 (1979), which is incorporated herein by reference), the arabinose promoter system, including the araBAD promoter (Guzman et al., J. Bacteriol., 174: 7716-7728 (1992), which is incorporated herein by reference; Guzman et al., J. Bacteriol., 177: 4121-4130 (1995), which is incorporated herein by reference; Siegele and Hu, Proc. Natl. Acad. Sci. USA, 94: 8168-8172 (1997), which is incorporated herein by reference), the rhamnose promoter (Haldimann et al., J. Bacteriol., 180: 1277-1286 (1998), which is incorporated herein by reference), the alkaline phosphatase promoter, a tryptophan (trp) promoter system (Goeddel, Nucleic Acids Res., 8: 4057 (1980), which is incorporated herein by reference), the PLtetO-1 and Plac/are-1 promoters (Lutz and Bujard, Nucleic Acids Res., 25: 1203-1210 (1997), which is incorporated herein by reference), and hybrid promoters such as the tac promoter. deBoer et al., Proc. Natl. Acad. Sci. USA, 80: 21-25 (1983), which is incorporated herein by reference. Non-limiting examples of mammalian and insect promoters can include CMV, SV40, LTR, and polyhedrin promoter.

An inducible promoter useful in the methods and systems as disclosed herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent may comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as disclosed herein can be a phage inducible promoter, nutrient inducible promoter, temperature inducible promoter, radiation inducible promoter, metal inducible promoter, hormone inducible promoter, steroid inducible promoter, and/or hybrids and combinations thereof. Appropriate environmental inducers can include, but are not limited to, exposure to heat (i.e., thermal pulses or constant heat exposure), various steroidal compounds, divalent cations (including Cu2+ and Zn2+), galactose, tetracycline, IPTG (isopropyl-β-D thiogalactoside), as well as other naturally occurring and synthetic inducing agents and gratuitous inducers.

Inducible promoters useful in the methods and systems as disclosed herein also include those that are repressed by "transcriptional repressors" that are subject to inactivation by the action of environmental, external agents, or the product of another gene. Such inducible promoters may also be termed "repressible promoters" where it is required to distinguish between other types of promoters in a given module or component of the biological switch converters described herein. Preferred repressors for use in the present invention are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline will cause the dissociation of the tet repressor from the engineered promoter and allow transcription of the sequence downstream of the engineered promoter to occur.

The cell comprising the nucleic acid can be, e.g. a microbial cell or a mammalian cell. In some embodiments, the cell as described herein is cultured under conditions suitable for the expression of the heme-binding composition polypeptide. Such conditions can include, but are not limited to, conditions under which the cell is capable of growth and/or polypeptide synthesis. Conditions may vary depending upon the species and strain of cell selected. Conditions for the culture of cells, e.g. prokaryotic and mammalian cells, are well known in the art. If the recombinant polypeptide is operatively linked to an inducible promoter, such conditions can include the presence of the suitable inducing molecule(s).

As used herein, "a Fc domain binding reagent" refers to an agent that is capable of binding specifically to a Fc domain. In some embodiments, a Fc domain binding reagent can be an anti-Fc antibody or a FcR receptor or portion thereof. The term "agent" refers generally to any entity which is normally not present or not present at the levels being administered to a cell. An agent can be selected from a group comprising: polynucleotides; polypeptides; small molecules; antibodies; or functional fragments thereof. As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity.

As used herein, "purifying" refers to the process of isolating a particular molecule or composition and/or treating a sample comprising a particular molecule or composition such that the molecule or composition is more isolated than before the treatment (e.g. is present at a higher level of purity). The term "isolated" or "partially purified" as used herein refers to a molecule or composition separated from at least one other component (e.g., nucleic acid or polypeptide) that is present with the molecule as found in its natural source and/or that would be present with the molecule when expressed by a cell, or secreted in the case of secreted polypeptides. A chemically synthesized nucleic acid or polypeptide or one synthesized using in vitro transcription/translation is considered "isolated."

In some embodiments, the polypeptides described herein can be purifying by means of a agent specific for one or more domains of the polypeptide, e.g. a substrate and/or antibody reagent that binds specifically to, e.g., Fc, a linker, a microbe-binding domain, etc.

In some embodiments, the methods described herein relate to treating a subject having or diagnosed as having sepsis with a method or composition described herein. Subjects having sepsis can be identified by a physician using current methods of diagnosing sepsis. Symptoms and/or complications of sepsis which characterize these conditions and aid in diagnosis are well known in the art and include but are not limited to, high fever, hot, flushed skin, elevated heart rate, hyperventilation, altered mental status, swelling, and low blood pressure. Tests that may aid in a diagnosis of, e.g. sepsis include, but are not limited to, blood cultures. Exposure to risk factors for sepsis (e.g. immunodeficiency) can also aid in determining if a subject is likely to have sepsis or in making a diagnosis of sepsis.

In some embodiments, the methods described herein comprise administering an effective amount of compositions described herein, e.g. a heme-binding molecule and/or composition to a subject in order to alleviate a symptom of sepsis and/or excess heme in the blood. As used herein, "alleviating a symptom of sepsis" is ameliorating any condition or symptom associated with the sepsis. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, injection, or cutaneous administration. Administration can be local or systemic.

In some embodiments, the methods described herein can comprise administering an effective amount of the compositions described herein, e.g. a heme-binding molecule and/or composition, to a subject in need of treatment for rhabdomyolysis (e.g., crush injury).

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the composition which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for the level of free heme in the blood of a subject, among others. The dosage can be determined by a physician and adjusted, as necessary, to suit observed effects of the treatment.

In some embodiments, the technology described herein relates to a pharmaceutical composition comprising a heme-binding molecule and/or composition as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. the heme-binding composition as described herein.

In some embodiments, the pharmaceutical composition comprising a heme-binding molecule and/or composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a heme-binding molecule and/or composition as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt can also be incorporated into the parenteral dosage forms of the disclosure, including conventional and controlled-release parenteral dosage forms.

The methods described herein can further comprise administering a second agent and/or treatment to the subject, e.g. as part of a combinatorial therapy. Non-limiting examples of a second agent and/or treatment can include antibiotics, fluid replacement, ultrafiltration, hemofiltration, dialysis, hemodialysis, hemodiafiltration, mechanical ventilation, insulin to control blood sugar levels, and vasopressors.

In some embodiments, treatment can comprise blood filtration of a subject in need of treatment for sepsis, as described above herein. In some embodiments, the filtration is performed extracoporeally.

In certain embodiments, an effective dose of a composition comprising a heme-binding molecule and/or composition as described herein can be administered to a patient, or the patient subjected to blood filtration using a heme-binding composition described herein, once. In certain embodiments, an effective dose of a composition comprising a heme-binding molecule and/or composition as described herein can be administered to a patient, or the patient subjected to blood filtration using a heme-binding composition described herein, repeatedly. For systemic administration, subjects can be administered a therapeutic amount of a composition comprising a heme-binding molecule and/or composition, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. sepsis by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to heme levels. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising a heme-binding molecule and/or composition can be administered over a period of time, such as over a 5 minute, 10 minute, 15 minute, 20 minute, or 25 minute period.

The dosage ranges for the administration of a heme-binding molecule and/or composition according to the methods described herein depend upon, for example, the form of the polypeptide, its potency, and the extent to which symptoms, markers, or indicators of a condition described herein are desired to be reduced, for example the percentage reduction desired for free heme levels in the blood. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a heme-binding molecule and/or composition in, e.g. the treatment of a condition described herein, or to induce a response as described herein (e.g. a decrease in free heme levels in the blood) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. the level of free heme in the blood. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. a decrease in free heme levels in the blood). It is well within the ability of one skilled in the art to monitor efficacy of administration and/or treatment by measuring any one of such parameters, or any combination of parameters. Efficacy can be assessed in animal models of a condition described herein, for example treatment of sepsis. When using an experimental animal model, efficacy of treatment is evidenced when a statistically significant change in a marker is observed, e.g. the level of free heme in the blood.

In vitro assays are provided herein which allow the assessment of a given dose of a composition. The efficacy of a given dosage combination can also be assessed in an animal model, e.g. an animal model of sepsis.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of sepsis. A subject can be male or female.

As used herein, "heme" refers to protoporhyrin IX (i.e. a compound having the structure of Formula I) bound to $Fe^{2+}$. In some embodiments, "heme" can additionally refer to hemin (i.e. the chloride salt of protoporphyrin IX-$Fe^{3+}$) and/or hematin (i.e. protoporphyrin IX-$Fe^{3+}$ hydroxide).

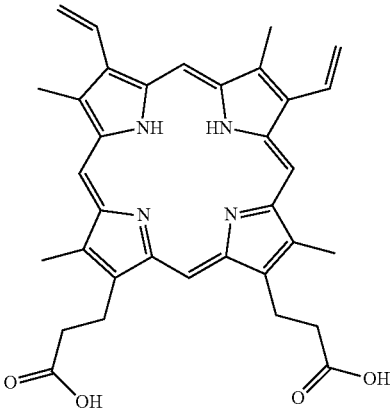

(Formula I)

As used herein, a "portion" refers to a part or fraction of a whole, e.g. a part or fraction of a total molecule. A particular molecule can have multiple portions, e.g. two portions, three portions, four portions, five portions, or more portions.

A subject can be one who has been previously diagnosed with or identified as suffering from or having a condition in need of treatment (e.g. sepsis) or one or more complications related to such a condition, and optionally, have already undergone treatment for sepsis or the one or more complications related to sepsis. Alternatively, a subject can also be one who has not been previously diagnosed as having sepsis or one or more complications related to sepsis. For example, a subject can be one who exhibits one or more risk factors for sepsis or one or more complications related to sepsis or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. sepsis. The term "treating" includes reducing or alleviating at least one adverse effect or symptom of a condition, disease or disorder associated with sepsis. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An engineered heme-binding molecule comprising a hemopexin domain and a second domain selected from the group consisting of:
   a linker; a microbe-binding molecule; and/or a substrate binding domain;
   wherein the second domain is conjugated to the hemopexin domain.
2. The engineered heme-binding molecule of paragraph 1, wherein the substrate binding domain is an Fc domain or AKT.
3. A heme-binding composition comprising a hemopexin domain conjugated to an Fc domain.
4. The molecule or composition of any of paragraphs 1-3, further comprising a detectable label.
5. A composition comprising the heme-binding molecule or heme-binding composition of any of paragraphs 1-4 and further comprising a microbe-binding domain.
6. The composition of paragraphs 1 or 5, wherein the microbe-binding domain is selected from the group consisting of:
   MBL and CRP.
7. The composition or molecule of any of paragraphs 1-6, further comprising a solid substrate or support to which the heme-binding molecule or composition is conjugated.
8. The composition or molecule of paragraph 7, wherein the solid substrate or support is a hollow fiber.
9. The heme-binding composition or molecule of any of paragraphs 1-8, wherein the hemopexin domain is a polypeptide comprising the sequence of SEQ ID NO: 2.
10. The heme-binding composition or molecule of any of paragraphs 1-9, wherein the hemopexin domain is a polypeptide having the sequence of SEQ ID NO: 2.
11. The heme-binding composition or molecule of any of paragraphs 1-8, wherein the hemopexin domain comprises a polypeptide having a sequence corresponding to residues 27-233 of SEQ ID NO: 2.
12. The heme-binding composition or molecule of any of paragraphs 1-8 wherein the hemopexin domain comprises a polypeptide having a sequence corresponding to residues 1-233 of SEQ ID NO: 2.
13. The heme-binding composition or molecule of any of paragraphs 1-8, wherein the hemopexin domain comprises a polypeptide having a sequence corresponding to residues 27-220 of SEQ ID NO: 2.
14. The heme-binding composition or molecule of any of paragraphs 1-8, wherein the hemopexin domain comprises a polypeptide having a sequence corresponding to residues 1-220 of SEQ ID NO: 2.
15. The heme-binding composition or molecule of any of paragraphs 1-8, wherein the hemopexin domain comprises a polypeptide having a sequence corresponding to residues 27-213 of SEQ ID NO: 2.
16. The heme-binding composition or molecule of any of paragraphs 1-8, wherein the hemopexin domain comprises a polypeptide having a sequence corresponding to residues 1-213 of SEQ ID NO: 2.
17. The heme-binding composition or molecule of any of paragraphs 1-16, wherein the hemopexin domain comprises a mutation wherein the residues corresponding to residues 220-226 of SEQ ID NO: 2 have been replaced with a polypeptide linker of about 1-10 amino acids in length.
18. The heme-binding composition or molecule of any of paragraphs 1-17, wherein the hemopexin domain comprises a mutation wherein the residues corresponding to residues 220-226 of SEQ ID NO: 2 have been replaced with the sequence GSGS (SEQ ID NO: 18).
19. The heme-binding composition or molecule of any of paragraphs 1-18, wherein the Fc domain is a polypeptide having the sequence of SEQ ID NO: 8, SEQ ID NO: 7, SEQ ID NO: 17.
20. A heme-binding composition of paragraph 3 having the sequence of SEQ ID NO: 4 or SEQ ID NO: 5.
21. A method of reducing the level of free heme in the blood of a subject, the method comprising contacting the blood of the subject with the heme-binding composition or molecule of any of paragraphs 1-20 or a molecule comprising a hemopexin domain.
22. A method of treating sepsis, the method comprising administering an effective amount of a heme-binding composition or molecule of any of paragraphs 1-20 or a molecule comprising a hemopexin domain.
23. A method of reducing the level of myoglobin in the blood of a subject, the method comprising contacting the blood of the subject with the heme-binding composition or molecule of any of paragraphs 1-20 or a molecule comprising a hemopexin domain.
24. A method of treating rhabdomyolysis or crush injury, the method comprising administering an effective amount of a heme-binding composition or molecule of any of paragraphs 1-20 or a molecule comprising a hemopexin domain.

25. The method of any of paragraphs 22 or 24, wherein the administration comprises contacting the blood of the subject with the heme-binding composition or molecule comprising a hemopexin domain.

26. The method of any of paragraphs 21-25, further comprising removing a portion of the subject's blood prior to the contacting step and performing the contacting step extracorporeally and then returning the portion of the subject's blood to the subject.

27. The method of paragraph 26, wherein the heme-binding composition or molecule comprising a hemopexin domain is bound to a solid substrate of an extracorporeal device.

28. The method of paragraph 27, wherein the solid substrate is a filter, affinity column, bear, or particle.

29. The method of any of paragraphs 21-28, wherein the molecule comprising a hemopexin domain is a molecule consisting essentially of a hemopexin domain.

30. The method of any of paragraphs 21-29, wherein the molecule comprising a hemopexin domain is a molecule consisting of a hemopexin domain.

31. The method of any of paragraphs 21-30, wherein the molecule comprising a hemopexin domain has the sequence of any of SEQ ID NOs: 1-2 or 9-16.

32. A method of producing a heme-binding composition or molecule, the method comprising:
  culturing a cell comprising a nucleic acid encoding a heme-binding composition or molecule of any of paragraphs 1-20 under conditions suitable for the production of proteins;
  and purifying the heme-binding composition or molecule by affinity purification with an stabilization domain binding reagent, ion exchange purification, or size based purification.

33. The method of paragraph 32, wherein the cell is selected from the group consisting of:
  a microbial cell; a mammalian cell; an insect cell; and a plant cell.

34. A method of producing a heme-binding molecule or composition, the method comprising:
  maintaining a nucleic acid encoding a heme-binding composition or molecule of any of paragraphs 1-20 under in vitro transcription and/or in vitro translation conditions suitable for the production of proteins;
  and purifying the heme-binding composition by affinity purification with an stabilization domain binding reagent, ion exchange purification, or size based purification.

EXAMPLES

Example 1: Fc Fusions to Hemopexin and Hemopexin Fragments for the Treatment of Sepsis Sepsis is a lethal condition that is often associated with a serious microbial infection. However, while many hypotheses have been put forward, the exact cause of septic shock is not agreed upon and therapeutics based on targeting the source of these various hypotheses have generally failed in (or prior to) clinical trials. Studies have recently suggested that excess free heme in the blood appears to play a role in the progression of sepsis and mechanism to remove the excess heme from blood could be very useful for patients suffering from sepsis. Host antimicrobial mechanisms reduce iron availability to pathogens. Iron proteins influencing the innate immune response include hepcidin, lactoferrin, siderocalin, haptoglobin, hemopexin, Nramp1, ferroportin and the transferrin receptor(1).

Under normal physiological conditions the protein hemopexin is responsible for binding free heme and activating the liver to remove the excess free heme from circulation. In a septic patient or animal, microbial infections can lead to a large increase in Red Blood Cell (RBS) lysis, which in turn leads to a significant increase in soluble free heme in the blood stream. This increase overwhelms the endogenous levels of hemopexin leading to dangerously high levels of heme. Excess heme in the blood provides microbial pathogens with a readily available source of iron, which can be limiting agent in microbial growth and hemoglobin and heme may substantially contribute to microbe-induced inflammation when bacterial or viral infection coexists with blood(2). In addition, free heme can have negative effects on an individual, although the exact mechanism has not been wholly determined.

At present there are no strategies to deal directly with high heme in the blood. The current treatment generally includes administration of antibiotics. Past clinical trials have focused on limiting the immune systems response to microbial infections, thereby reducing the "Cytokine Storm" that has been hypothesized to be the causative agent of sepsis. In addition, people have looked to use dialysis to remove soluble cytokines—also to remove cytokines.

Described herein are Fc fusions to endogenous or engineered versions of endogenous proteins to target heme for removal without introducing an immunogenic agent. Both full-length hemopexin and the amino terminal domain of hemopexin have been shown to bind heme with binding constants of 1 pM and 1 nM respectively. Described herein is the design and production of an Fc fusion to full-length human hemopexin, Fc fusions to multiple fragments of the N-terminal domain of human hemopexin and an Fc fusion to full length hemopexin where the linker connecting the two structural domains is replaced with a different polypeptide linker.

Expression and purification of recombinant versions of many endogenous proteins can be difficult and most experiments with hemopexin have used hemopexin purified from blood(3).

Sequences of Fc-Hemopexin Fusions:
>aktFcHemopexin; A fusion protein of the following motifs listed from N-terminus to C-terminus: the tripeptide Ala-Lys-Thr, the neck and Fc region of human IgG1 (N297D), a single alanine insertion, human hemopexin (with the leader sequence removed) (SEQ ID NO:3).

AKTEPKSSDKTHTCPPCPAPELLGGPSVFLFPPKPKDTLMISRTPEVTC

VVVDVSHEDPEVKFNWYVDGVEVHNAKTKPREEQYDSTYRVVSVLTVLH

QDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYS

KLTVDKSRWQQGNVFSCSVMHEALHNHYTQKSLSLSPGATPLPPTSAHG

NVAEGETKPDPDVTERCSDGWSFDATTLDDNGTMLFFKGEFVWKSHKWD

RELISERWKNFPSPVDAAFRQGHNSVFLIKGDKVWVYPPEKKEKGYPKL

LQDEFPGIPSPLDAAVECHRGECQAEGVLFFQGDREWFWDLATGTMKER

SWPAVGNCSSALRWLGRYYCFQGNQFLRFDPVRGEVPPRYPRDVRDYFM

PCPGRGHGHRNGTGHGNSTHHGPEYMRCSPHLVLSALTSDNHGATYAFS

-continued
GTHYWRLDTSRDGWHSWPIAHQWPQGPSAVDAAFSWEEKLYLVQGTQVY

VFLTKGGYTLVSGYPKRLEKEVGTPHGIILDSVDAAFICPGSSRLHIMA

GRRLWWLDLKSGAQATWTELPWPHEKVDGALCMEKSLGPNSCSANGPGL

YLIHGPNLYCYSDVEKLNAAKALPQPQNVTSLLGCTH

>aktFcHemopexinNT: A fusion protein of the following motifs listed from N-terminus to C-terminus: the tripeptide Ala-Lys-Thr, the neck and Fc region of human IgG1 (N297D), a single alanine insertion, the N-terminal domain of human hemopexin (residues 24-256 of the expressed protein) (SEQ ID NO: 4).

AKTEPKSSDKTHTCPPCPAPELLGGPSVFLFPPKPKDTLMISRTPEVTC

VVVDVSHEDPEVKFNWYVDGVEVHNAKTKPREEQYDSTYRVVSVLTVLH

QDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYS

KLTVDKSRWQQGNVFSCSVMHEALHNHYTQKSLSLSPGATPLPPTSAHG

NVAEGETKPDPDVTERCSDGWSFDATTLDDNGTMLFFKGEFVWKSHKWD

RELISERWKNFPSPVDAAFRQGHNSVFLIKGDKVWVYPPEKKEKGYPKL

LQDEFPGIPSPLDAAVECHRGECQAEGVLFFQGDREWFWDLATGTMKER

SWPAVGNCSSALRWLGRYYCFQGNQFLRFDPVRGEVPPRYPRDVRDYFM

PCPGRGHGHRNGTGHGNSTHHGPEYMR

The AKT tripeptide at the N-terminus of the Fc permits site-specific modification of the protein and is optional. The N297D mutation generates an agylcosylated version of the Fc fragment, the wild type asparagine (N297) can be used depending on the glycosylation state desired for expression and Fc Receptor interactions.

Expression and Purification of Fc-Hemopexin fusions. The above genes were cloned into a mammalian expression vector and transfected into 293F cells (Invitrogen). Five days later the supernatant was collected and loaded onto a Protein A column (GE). Fc containing proteins bound to Protein A were eluted in low pH buffer and neutralized to pH 7. The amount of purified protein was quantified and run on an SDS gel to confirm its purity (Table 1 and FIG. 1).

TABLE 1

| Protein | Predicted MW | Yield (per liter of cell culture) |
|---|---|---|
| FcHemopexin | 76 kDa | 17 mg |
| FcHemopexin-NT | 53 kDa | 30 mg |
| FcHemopexin-G220 | 51 kDa | 15 mg |

TABLE 1-continued

| Protein | Predicted MW | Yield (per liter of cell culture) |
|---|---|---|
| FcHemopexin-H213 | 51 kDa | 10 mg |
| FcHemopexin-T24 | 73 kDa | 1 mg |
| Hemopexin_G220H226GSGS | 75 kDa | 4 mg |

Figure 2:
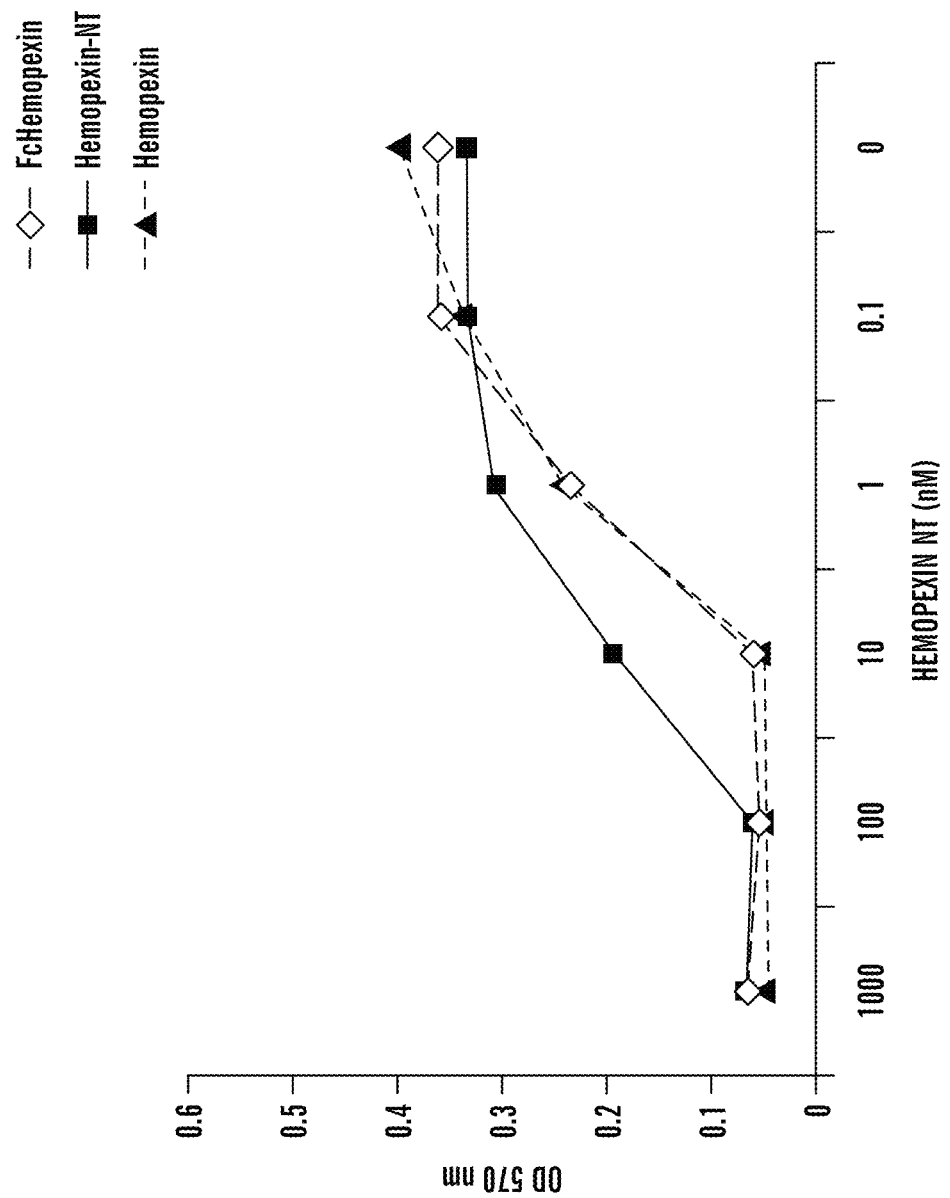
FIG. 2 depicts a graph of Fc-Hemopexin and Fc-Hemopexin-NT binding to free hemin.
Figure 4:
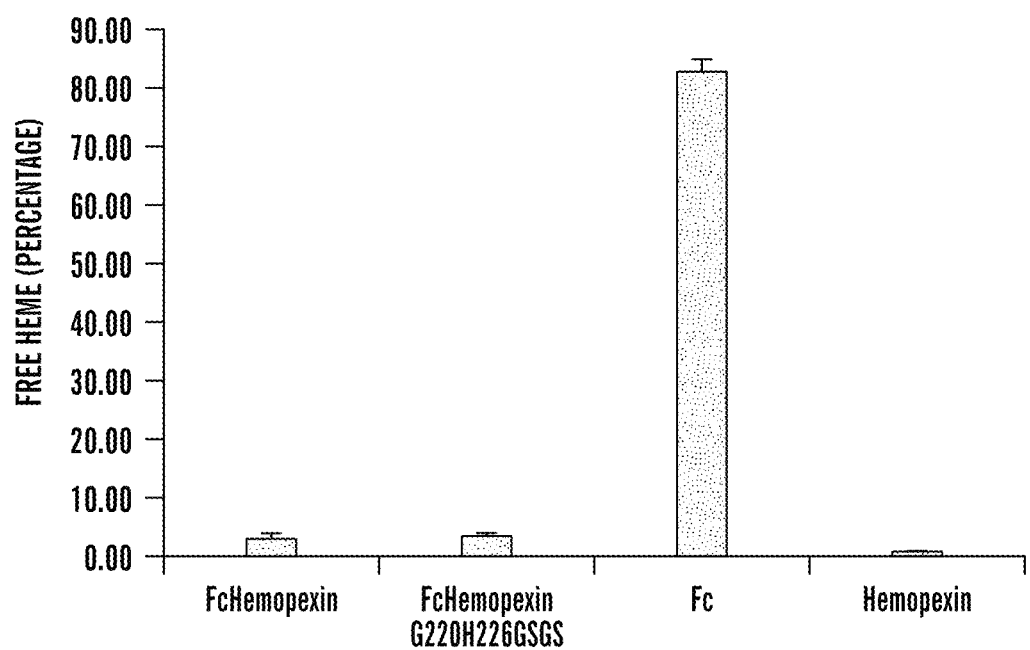
FIG. 4 depicts a graph of heme binding of Fc Fusions with variants of Full Length Hemopexin was also determined.
Figure 5:
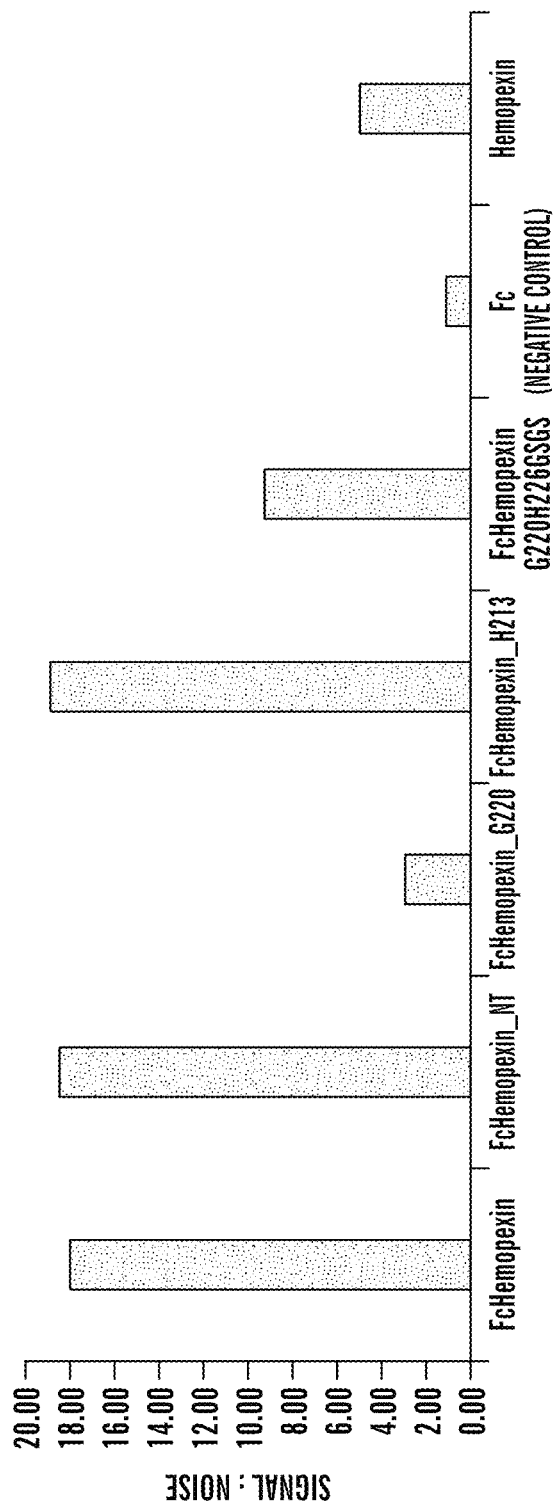
FIG. 5 depicts a graph of FcHemopexin variants binding to myoglobin.

Binding of Fc-Hemopexin fusions to free Hemin (Hemin is a chloride ion of heme). Fc-Hemopexin, Fc-Hemopexin-NT, FcHemopexin-G220, FcHemopexin-H213 and FcHemopexin-G220H226GSGS all bind free hemin and the binding of hemin to Fc-Hemopexin is indistinguishable from hemin binding to native human Hemopexin (FIGS. 2, 4, and 5).

REFERENCES

1. E. E. Johnson, M. Wessling-Resnick, Iron metabolism and the innate immune response to infection. *Microbes and infection/Institut Pasteur* 14, 207 (March, 2012).
2. T. Lin et al., Synergistic inflammation is induced by blood degradation products with microbial Toll-like receptor agonists and is blocked by hemopexin. *The Journal of infectious diseases* 202, 624 (Aug. 15, 2010).
3. M. R. Mauk, A. Smith, A. G. Mauk, An alternative view of the proposed alternative activities of hemopexin. Protein science: a publication of the Protein Society 20, 791 (May, 2011).
4. K. M. Lo et al., High level expression and secretion of Fc-X fusion proteins in mammalian cells. Protein engineering 11, 495 (June, 1998).

Example 2

Different FcHx contructs' binding to Myoglobin were determined (Table 2).

The polypeptides described in Table 2 were fused to the C-terminus of SEQ ID NO: 17, which comprises the Fc fragment of human IgG with an alanine-lysine-threonine tripeptide on the N-terminus and a single alanine on the C-terminus. Table 2 summarizes the expression and binding data from these proteins.

Figure 3:
FIG. 3 depicts a graph of the heme binding of Fc fusions with variants of the N-terminal domain of Hemopexin.

The heme Binding of Fc fusions with variants of the N-terminal domain of Hemopexin was determined (FIG. 3). Free Heme was incubated with the specified protein and then Free Heme was detected indirectly using an enzymatic heme dependent peroxidase reaction. Heme Binding of Fc Fusions with variants of Full Length Hemopexin was also determined (FIG. 4).

FcHemopexin variants' binding to myoglobin was determined (FIG. 5). Myoglobin was coated in assay wells and then incubated with various protein probes, including the Fc Hemopexin fusions, the Fc alone (negative control), recombinant hemopexin and an anti-myoglobin antibody (positive control). The binding of the protein probe was then assayed using a horse radish peroxidase detection system and the data for each protein probe was compared to wells coated with no Myoglobin.

TABLE 2

| Fc fusion Protein | SEQ ID NO: | Starting Reside* | Last Residue* | Expression | Heme Binding | Myoglobin Binding |
|---|---|---|---|---|---|---|
| Hemopexin | 1 | 1 | 439 | + | + | + |
| HemopexinNT | 9 | 1 | 233 | + | + | + |
| Hemopexin_T24 | 10 | 24 | 439 | + | NA | NA |
| Hemopexin_S28 | 11 | 28 | 439 | − | NA | NA |
| HemopexinNT_G220 | 12 | 1 | 220 | + | + | + |
| HemopexinNT_H213 | 13 | 1 | 213 | + | + | + |

TABLE 2-continued

| Fc fusion Protein | SEQ ID NO: | Starting Reside* | Last Residue* | Expression | Heme Binding | Myoglobin Binding |
|---|---|---|---|---|---|---|
| HemopexinNT_G212 | 14 | 1 | 212 | − | NA | NA |
| HemopexinNT_P207 | 15 | 1 | 207 | − | NA | NA |
| Hemopexin_mut3 G220H226GSGS** | 16 | 1 | 439 | + | + | + |

*Starting and Ending residues use the numbering system of mature human hemopexin
**Residues from gly 220 to thr 219 replaced with a gly-ser-gly-ser (SEQ ID NO: 18) linker The general ELISA reagents and conditions were as follows: Wash buffer: PBS-T (175 ul×6); Incubation buffer: PBS; Pre-block=1% Milk and PBS (RT for 1 hr); Incubation with Protein (RT for 1 hr); Antibody-HRP buffer=0.5% Milk in PBS (RT for 1 hr).

What is claimed herein is:

1. An engineered heme-binding molecule comprising a heme-binding domain of human hemopexin and a human IgG Fc domain; wherein the heme-binding domain is conjugated to the Fc domain; wherein the heme-binding domain comprises a polypeptide that is at least 90% identical to a sequence corresponding to residues 27-213 of SEQ ID NO: 2; and wherein the heme-binding domain binds to heme.

2. The engineered heme-binding molecule of claim 1, wherein the heme-binding domain is at the N terminal of the Fc domain.

3. The engineered heme-binding molecule of claim 1, wherein the heme-binding domain is at the C terminal of the Fc domain.

4. The engineered heme-binding molecule of claim 1, further comprising a detectable label.

5. The engineered heme-binding molecule of claim 1 further comprising a microbe-binding domain.

6. The engineered heme-binding molecule of claim 5, wherein the microbe-binding domain is selected from the group consisting of:
   mannose-binding lectin (MBL) and C-reactive protein (CRP).

7. The engineered heme-binding molecule of claim 1, wherein the heme-binding domain comprises a polypeptide that is at least 90% identical to a sequence corresponding to:
   a) SEQ ID NO: 2;
   b) residues 27-233 of SEQ ID NO: 2;
   c) residues 1-233 of SEQ ID NO: 2;
   d) residues 27-220 of SEQ ID NO: 2;
   e) residues 1-220 of SEQ ID NO: 2; or
   f) residues 1-213 of SEQ ID NO: 2.

8. The engineered heme-binding molecule of claim 1, wherein the heme-binding domain comprises a mutation wherein the residues corresponding to residues 220-226 of SEQ ID NO: 2 have been replaced with a polypeptide linker of about 1-10 amino acids in length.

9. The engineered heme-binding molecule of claim 1, wherein the heme-binding domain comprises a mutation wherein the residues corresponding to residues 220-226 of SEQ ID NO: 2 have been replaced with the sequence GSGS (SEQ ID NO: 18).

10. The engineered heme-binding molecule of claim 1, wherein the Fc domain is a polypeptide having the sequence of SEQ ID NO: 8, SEQ ID NO: 7 or SEQ ID NO: 17.

11. The engineered heme-binding molecule of claim 1 having the sequence of SEQ ID NO: 3, SEQ ID NO: 4 or SEQ ID NO: 5.

12. The engineered heme-binding molecule of claim 1, further comprising a linker or a substrate-binding domain.

13. The engineered heme-binding molecule of claim 12, wherein the substrate-binding domain comprises alanine-lysine-threonine (AKT) (SEQ ID NO: 35).

14. The engineered heme-binding molecule of claim 1, wherein the heme-binding domain comprises a polypeptide that is at least 90% identical to a sequence corresponding to:
   a. residues 24-462 of SEQ ID NO: 1;
   b. residues 24-256 of SEQ ID NO: 1;
   c. residues 27-233 of SEQ ID NO: 1;
   d. residues 1-233 of SEQ ID NO: 1;
   e. residues 27-220 of SEQ ID NO: 1;
   f. residues 1-220 of SEQ ID NO: 1;
   g. residues 27-213 of SEQ ID NO: 1;
   h. residues 1-213 of SEQ ID NO: 1;
   i. residues 27-256 of SEQ ID NO: 1; or
   j. residues 1-256 of SEQ ID NO: 1.

15. The engineered heme-binding molecule of claim 1, wherein the heme-binding domain binds to heme and the Fc domain binds to an Fc receptor, thereby reducing the level of free heme or reducing the level of a molecule comprising heme in a solution.

16. The engineered heme-binding molecule of claim 15, wherein the level of free heme or the level of the molecule comprising heme is reduced by at least 20%.

17. The engineered heme-binding molecule of claim 15, wherein the level of free heme or the level of the molecule comprising heme is reduced by at least 95%.

18. The engineered heme-binding molecule of claim 15, wherein the solution is blood.

* * * * *